United States Patent
De Strooper et al.

(10) Patent No.: US 10,377,834 B2
(45) Date of Patent: *Aug. 13, 2019

(54) SINGLE DOMAIN ANTIBODIES CAPABLE OF MODULATING BACE ACTIVITY

(71) Applicants: VIB VZW, Ghent (BE); Katholieke Universiteit Leuven, K.U. Leuven R & D, Leuven (BE); Vrije Universiteit Brussel, Brussels (BE)

(72) Inventors: Bart De Strooper, Leuven (BE); Els Marjaux, Attenrode-Wever (BE); Lujia Zhou, Leuven (BE); Serge Muyldermans, Hoeilaart (BE)

(73) Assignees: VIB VZW, Ghent (BE); KATHOLIEKE UNIVERSITEIT LEUVEN. K.U. LEUVEN R&D, Leuven (BE); VRIJE UNIVERSITEIT BRUSSEL, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/872,498

(22) Filed: Jan. 16, 2018

(65) Prior Publication Data

US 2018/0230232 A1 Aug. 16, 2018

Related U.S. Application Data

(63) Continuation of application No. 14/023,586, filed on Sep. 11, 2013, now Pat. No. 9,908,943, which is a continuation of application No. 12/736,389, filed as application No. PCT/EP2009/053985 on Apr. 3, 2009, now Pat. No. 8,568,717.

(60) Provisional application No. 61/041,965, filed on Apr. 3, 2008.

(51) Int. Cl.
*C07K 16/40* (2006.01)

(52) U.S. Cl.
CPC .......... *C07K 16/40* (2013.01); *C07K 2317/22* (2013.01); *C07K 2317/565* (2013.01); *C07K 2317/569* (2013.01); *C07K 2317/76* (2013.01); *C07K 2317/92* (2013.01)

(58) Field of Classification Search
CPC ............ C07K 2317/92; C07K 2317/76; C07K 2317/565; C07K 16/40; C07K 2317/569; C07K 2317/22
See application file for complete search history.

(56) References Cited

U.S. PATENT DOCUMENTS

| 5,693,761 A | 12/1997 | Queen et al. |
| 5,766,886 A | 6/1998 | Studnicka et al. |
| 5,821,123 A | 10/1998 | Studnicka |
| 5,859,205 A | 1/1999 | Adair et al. |
| 5,869,619 A | 2/1999 | Studnicka |
| 6,054,297 A | 4/2000 | Carter et al. |
| 6,180,370 B1 | 1/2001 | Queen et al. |
| 2006/0034848 A1 | 2/2006 | Kinoshita |

FOREIGN PATENT DOCUMENTS

| EP | 0 626 390 A1 | 11/1994 | |
| WO | 94/04678 A1 | 3/1994 | |
| WO | 99/37681 A2 | 7/1999 | |
| WO | 00/43507 A1 | 7/2000 | |
| WO | 01/90190 A2 | 11/2001 | |
| WO | 02/085945 A2 | 4/2002 | |
| WO | 02/47466 A2 | 6/2002 | |
| WO | 02/057445 A1 | 7/2002 | |
| WO | 03/025020 A1 | 3/2003 | |
| WO | 03/035694 A2 | 5/2003 | |
| WO | 2004/049794 A2 | 6/2004 | |
| WO | 2006/040153 A2 | 4/2006 | |
| WO | 2006/040154 A2 | 4/2006 | |
| WO | WO-2009033743 A1 * | 3/2009 | ............ C07K 16/18 |
| WO | 2009/121948 A2 | 10/2009 | |

OTHER PUBLICATIONS https://en.wikipedia.org/wiki/Ectodomain, retrieved Jul. 14, 2016.
Choy et al., "Amyloid Precursor Protein (APP) Traffics from the Cell Surface via Endosomes for Amyloid β (Aβ) Production in the Trans-Golgi Network," Jun. 18, 2012, PNAS, pp. E2077-E2082.
Conrath et al., "β-Lactamase Inhibitors Derived from Single-Domain Antibody Fragments Elicited in the Camelidae," Antimicrobial Agents and Chemotherapy, Oct. 2001, pp. 2807-2812, vol. 45, No. 10.
Harmsen N M et al., "Properties, Production, and Applications of Camelid Single-Domain Antibody Fragments," Applied Microbiology and Biotechnology, Aug. 18, 2007, pp. 13-22, Springs, Berlin, Germany, vol. 77, No. 1.
Hussain et al., "Oral Administration of a Potent and Selective Non-Peptidic BACE-1 Inhibitor Decreases β-Cleavage of Amyloid Precursor Protein and Amyloid-β Production in Vivo," Journal of Neurochemistry, 2007, pp. 802-809, vol. 100, No. 3.
Kolkman et al., "Nanobodies—from Llamas to Therapeutic Proteins," 2010, Drug Discovery Today, vol. 7, No. 2.
Marjaux et al., "γ-Secretase Inhibitors: Still in the Running as Alzheimer's Therapeutics," Drug Discovery Today: Therapeutic strategies, Sep. 1, 2004. pp. 1-6, vol. 1, No. 1.

(Continued)

*Primary Examiner* — Gregory S Emch

(74) *Attorney, Agent, or Firm* — Kilpatrick Townsend & Stockton LLP

(57) ABSTRACT

Described are single domain antibodies with a specificity for BACE1. More specifically, described are single variable-domain antibodies derived from camelids that bind to BACE1 and are capable of inhibiting the activity of BACE1. The antibodies can be used for research and medical applications. Specific applications include the use of BACE1-specific antibodies for the treatment of Alzheimer's disease.

9 Claims, 9 Drawing Sheets

Specification includes a Sequence Listing.

(56) References Cited

OTHER PUBLICATIONS

Martin et al., "Intracellular Accumulation of fl-Amyloid in Cells Expressing the Swedish Mutant Amyloid Precursor Protein," Sep. 20, 1995, The Journal of Biological Chemistry.
Muruganandam et al., "Selection of Phage-Displayed Llama Single-Domain Antibodies that Transmigrate across Human Blood-Brain Barrier Endothelium," FASEB J. Feb. 2002; 16(2):240-2, Epub Dec. 28, 2001.
Paul, W. E., "Fundamental Immunology," Third Edition, 1993, pp. 292-295.
PCT International Search Report; PCT/EP2009/053985; dated Nov. 23, 2009.
Rudikoff et al., "Single Amino Acid Substitution Altering Antigen-Binding Specificity," Proc Nat'l Acad Sci USA, Mar. 1982; 79(6):1979-83.
Sannerud et al., "ADP Ribosylation Factor 6 (ARF6) Controls Amyloid Precursor Protein (APP) Processing by Mediating the Endosomal Sorting of BACE1," Aug. 23, 2011, PNAS, vol. 108, No. 34, pp. E559-E568.
Thinakaran et al., "Metabolism of the Swedish Amyloid Precursor Protein Variant in Neuro2a (N2a) Cells," Feb. 8, 1996, The Journal of Biological Chemistry, vol. 271, No. 16, Issue of Apr. 19, pp. 9390-9397.
Vassar et al., β-Secretase Cleavage of Alzheimer's Amyloid Precursor Protein by the Transmembrane Aspartic Protease BACE, Science, Oct. 22, 1999, pp. 735-741, vol. 286.
Wesolowski et al., "Single Domain Antibodies: Promising Experimental and Therapeutic Tools in Infection and Immunity," Med Microbiol Immunol. Aug. 2009; 198(3): 157-74. Doi 10.1007/s00430-009-0116-7. Epub Jun. 16, 2009.
Yan et al., "Targeting the β Seretase BACE1 for Alzheimer's Disease Therapy," Lancet Neurology, 13(3), 319-329, 2014.

* cited by examiner

FIG. 1

```
              < -- Framework-1 -- > < - CDR1 - > < Framework-2 > < --- CDR2 --- >

5    10    15    20    25    30    35     40    45      50  a b 55    60    65
                  |    |     |     |     |     |     |      |     |       |   |||    |     |

Nb_B1    DVQLQESGGGSVQAGGSLRLSCVAS  GWTYSSNSLSMA   WFRQAPGKEREGVA  --TI-TSYVGRTYYADSVKG
      NB_B2    DVQLQESGGGSVQAGGSLRLSCAVS  GFSYS--PYYMG   WFRQAPGKEREGVA  --AI-RKGIGTTYYADSVKG
      Nb_B3    DVQLQESGGGSVQAGGSLRLSCAVS  GYTYN--IYTMA   WFRQAPGKEREGVA  --GIY-SPGGTTYYADSVKG
      Nb_B5    DVQLQESGGGSVQAGGSLRLSCAAS  GYTFT--KYPMG   WFRQAPGKECFLVS  --SI-TS-GGVTTYASSVKG
      Nb_B8    DVQLQESGGGSVQAGGSLRLSCARS  GGTVS--TPYMA   WFRQGPGKERFGVA  --AIYD-GRAKT-YAGSLQG
      Nb_B9    DVQLQESGGGSVQAGGSLRLSCAAS  EYTYG--YCSMG   WYRQAPGKERELVS  --TI-TSDGS-TSYVDSVKG
      Nb_B10   DVQLQESGGGSVQPGGSLRLSCAAS  GYFYS--RWYMG   WFRQAPGKEREGVA  --AI-NSGGSITSYADSVKG
      Nb_B11   DVQLQESGGGSAQAGGSLRLSCEVS  GYTYS---GYFMG  WFRQAPGEEREGVA  --AI-DTNGGRTWYADSVKG
      Nb_B12   DVQLQESGGGSVQAGGSLRLSCVAS  GFTYR---RYFMG  WFRQAPGKEREAVA  ---TM-FSCGGTTYYADSVKG
      Nb_B15   DVQLQESGGGSVQAGGSLRLSCAAS  GYSYS----YYIG  WFRQAPGKEREGVA  AIAIVNSGGGRTYYADSVKG
      Nb_B16   DVQLQESGGGSVQAEGSLRLSCTAS  GYTYS-----LMG  WFRQAPGKEREGVA  --VI-NSGVGTTYYADSVKG
      Nb_B21   DVQLQESGGGSVQAGGSLRLSCAAS  GYTSE---MNRFA  WLRQAPGKDREVVA  --VIFPTARGAKFYSDSVNG
      Nb_B25   QVQLQESGGGTVQAGGSLRLSCAAS  GYTYR---SYCMG  WFRQAPGKEREEVA  --SI-NSDQGSTRYAASVKG
      Nb_B26   DVQLQESGGGSVQAGGSLRLSCAAS  GYAFS---SYYMG  WFRQAPGREREEVT  --GI-TQIGGTTYYADSVKG

Nb_B4    DVQLQESGGGLVQPGGSLRLSCAAS  EFTFG---SYWMY  WVRQAPGKGLEWVA  --QI-NARGSTIYYVDSVKG
      Nb_B6    DVQLQESGGGLVRPGGSLRLSCAAS  GFTFA---NYWLY  WVRDAPGKGIEWVS  --QI-GPSGRSTYYADAVKG
      Nb_B7    DVQLQESGGGLVQPGGSLRLSCAAS  GFAFS---SYWMY  WVRQAPGKGLEWVS  --QV-NSDGGSTYYVDSVKG
      Nb_B13   DVQLQESGGGLVQPGGSLRLSCAAS  GFTFS---SYWMY  WVRQAPGKGLEWVS  --QI-NSSGGTTYYADSVKG
      Nb_B14   DVQLQESGGGLVQPGGSLRLSCAAS  GFTFS---NYWMY  WVRQAPGKGLEWVS  --QI-DGGGRKTYYADSLKG
      Nb_B24   DVQLQESGGGLVQPGGSLRLSCAAS  GFPFS---VYWMY  WVRQAPGKGLEWVS  --QI-DSGGYTTYYTDSVKG
```

FIG. 1 continued

```
<      ------ Framework-3 ------   >   <  ----- CDR3 -----  >   Framework-4
   70    75    80 abc 85    90                                    105   110
    |     |     |  |||  |    |                                      |    |

RFTISRDHAKST--VYLQIDSLKPEDTATYYCAA    EYLGGS--FLSTGA---------YKY    WGQGTQVTVSS    Nb_B1
RFTFSQDDAKNT--MYLQMNSLKPEDTAIYFCAV    GHYRAYATTSFDPRR------YDY      WGQGTQVTVSS    Nb_B2
RFTISQDNAKNT--VYLQMNSLAPEDTAIYYCAA    RGGLLSRVLKEAG--------YNA      WGQGTQVTVSS    Nb_B3
RFTISRDNAKNT--VYLQMNSLKPEDTAVYYCAA    QYPYSSSWER---CPFR---IGY       WGQGTQVTVSS    Nb_B5
RFTISQDNDKNT--LYLQMNSLKPDDTAVYYCAA    GNGGGNWL----RPSE------YNY     WGKGTQVTVSS    Nb_B8
RFTISQDNAKNT--VYLQMNSLKPEDTAKYYCYT    KTCA--NK--LGAK---------FIS    WGQGTQVTVSS    Nb_B9
RFTISQDNAKNT--VYLQMNSLKPEDTAIYYCAA    ALSRVPGFFP---LFPSQ--YNY       WGQGTQVTVSS    Nb_B10
RFTISHDNAEST--VYLQMNSLQPEDTAIYFCAA    RRPPGGSWYPPP---LRKYSYNF       WGQGTQVTVSS    Nb_B11
RFTATQDNAKNT--VYLQMNNLKPEDTAIYYCAA    ASGCWYDGSPAA-----RSVDVSF      WGHGTQVTVSS    Nb_B12
RFTISQCNDKNT--VYLQMNSLKPEDTAIYYCAA    RSLSWYSHPL----LQPSQ---FNN     WCQCTQVTVSS    Nb_B15
RFTISQNAKST--VYLQMNSLKPEDTAIYYCAA     RRSWFTGMTTTQALDPDW---FSY      WGQGTQVTVSS    Nb_B16
RFTISQDTAKNT--VYLQMNSLEPDTAMYFCAA     SANAMTGFQPSG---------YTY      WGQGTQVTVSS    Nb_B21
RFTSSQDNANNTVTVYLQMNSLKPEDTAIYYCAA    NDGCAYRVYRGGAYG------YNF      WGQGTQVTVSS    Nb_B25
RFTISRDNAKNT--VYLQMDSLKPEDTAIYYCAK    LRRPFYYPLLERPSEGD---FDY       WGQGTQVTVSS    Nb_B26

RFTISRDNAKNT--LYLQMNSLKPEDTAVYYCAT    DSRGTH---------------         KGQGTQVTVSS    Nb_B4
RFTISRDNAKNT--LYLQMNSLKPEDSAVYYCAT    SSGGNE---------------         RGQGTQVTVSS    Nb_B6
RFTISRDNAKNT--LYLHMNSLKPEDTAVYYCAT    DSSGRY---------------         RGQGTQVTVSS    Nb_B7
RFTISRDNAKNT--LYLQMNSLKPEDTAVYYCAT    GSAGQG---------------         KGQGTQVTVSS    Nb_B13
RFTISRDNAKNT--LYLQMNSLKPEDTAMYYCAT    DSAGSH---------------         RGQGTQVTVSS    Nb_B14
RFSASRDNSKNT--LYLQMNSLKPEDTAVYYCAT    DSIGSN---------------         KGQGTQVTVSS    Nb_B24
```

FIG. 3
A
B
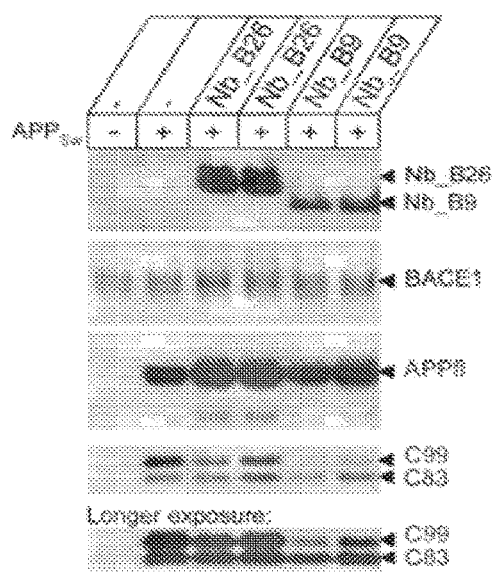
C
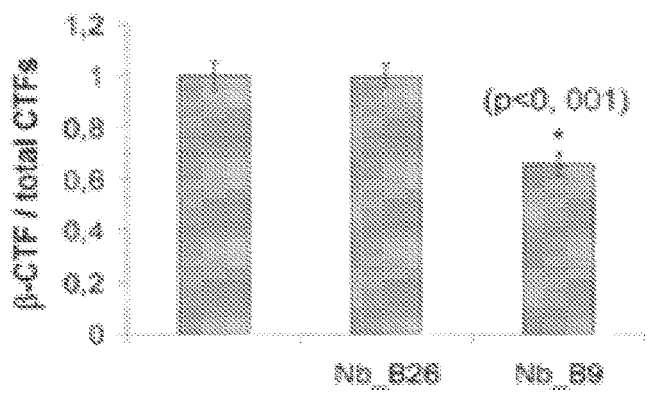

FIG. 4

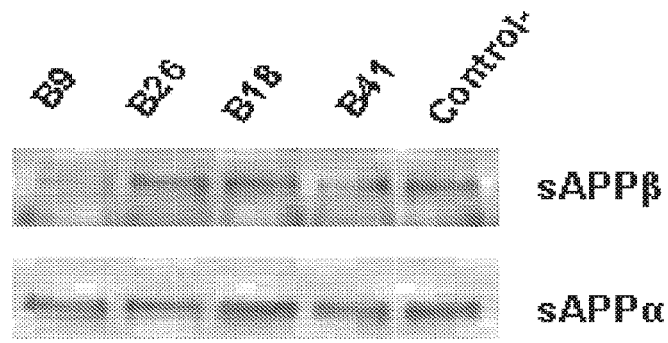

sAPPβ sAPPα

FIG. 5

```
              <-----Framework1----->  < -CDR1- >  < Framework2 >  < -------CDR2----->
Nb_B9         DVQLQESGGGSVQAGGSLRLSCAAS  EYTYGYC-SMG  WYRQAPGKERELVS  TITSDGS-TS-YVESVKG
Nb_1B3        QVQLQESGGGSVQAGGSLRLSCAAS  EYTDSTY-YMA  WFRQAPGKERGGVA  TLASRYD-TTYYADSVKG
Nb_10C2       QVQLQESGGGSVQAGGSLRLSCAAS  RDILTLY-YMG  WFRQAPGKEREGVA  AISSDII-FTSYANSVKG
Nb_12B6       QVQLQESGGGSVQAGGSLRLSCAAS  RDILTLY-YMG  WFRQAPGKEREGVA  AISSDII-FTSYANSVKG
Nb_10B5       QVQLQESGGGSVQAGGSLRLSCAHS  ---NTYPTYMG  WFRQAPGKEREGVA  AIYTGDG-TTYYGDSVKG
Nb_13A5       QVQLQESGGGSVQAGGSLRLSCAHS  ---NTYPTYMG  WFRQAPGKEREGVA  AIYTGDG-TTYYGDSVKG
Nb_2C6        QVQLQESGGGSVQAGGSLRLSCAAS  GFTSSVY-YIS  WFRQAPGKEREGVA  AINSGGG-ITFYADSVKG
Nb_6A4        QVQLQESGGGLVQPGGSLRLSCAAS  GFTFSNY-WMY  WVRQAPGKGLEWVS  QINSGGG-TTYSTDSVKG
Nb_10C4       QVQLQESGGGSVQAGGFLRLSCAAS  GYTYSTC-SMA  WYRQAPGKERELVS  SI--RNDGSTAYADSVKG
Nb_13B6       QVQLQESGGGSVQAGGSLRLSCAAS  GISRSTY-FMG  WFRQAPGKEREGVA  VINYGTT-TPYYPDSVKG
Nb_1A4        QVQLQESGGGSVQAGGSLRLSCAAS  GATASDY-CMG  WFRQAPGKEREGVA  AI-SRGG-MTYHVDSVRG
Nb_2B6        QVQLQESGGGSVQAGGSLRLSCAAS  GRIF-DLRDMG  WYRQVPGKQRELVA  AI-TSGG-TSNYADSVKG
Nb_4A2        QVQLQESGGGLVQPGGSLRLSCAAS  GFTFETQ-YMT  WVRQAPGKGPEYVS  SINSGGTIKYYANSSVKG
Nb_1D4        QVQLQESGGGLVQPGGSLRLSCAAS  GFTFSTY-WMY  WVRQAPGKGLEWVS  AISTEGGS-TRYAGSVKG
Nb_9D3        QVQLQESGGGLVQPGGSLRLSCAAS  GFTFSSY-WMY  WFRQAPGKGLERVS  AINFGGDV-TYYTDSVKG <---------Framework2-----------> < -----CDR3----- >  <Framework3>
              RFTISQDNAKNTVYLQMNSLKPEDTAKYYCYT  KTCANKLGAKFI-----S  WGQGTQVTVSS   Nb_B9
              RFTISQDNAKNTVYLQMNSLKPEDTGIYYCAA  SPRR-PGFFPLDPSQYNY  WGQGTQVTVSS   Nb_1B3
              RFTISRDKDKNTVYLQMNSLKPEDTAIYYCAA  ASTWVPGFFPLFASQYNS  WGQGTQVTVSS   Nb_10C2
              RFTISRDEDKNTVYLQMNSLKPEDTAIYYCAA  ASTWVPGFFPLFASQYNS  WGQGTQVTVSS   Nb_12B6
              RFTISQDNAKNTVYLQMNSLKPEDTAIYYCAA  ALSRVPGFFPLFPSQYNY  WGQGTQVTVSS   Nb_10B5
              RFTISQDNAKNTVYLQMNSLKPEDTAIYYCAA  ALSRVPGFFPLFPSQYNY  WGQGTQVTVSS   Nb_13A5
              RFTISQDNAKNTVYLQMNSLKPEDTAIYYCAA  ALSRVPGFFPLFPSQYNS  WGQGTQVTVSS   Nb_2C6
              RFTISRDNAKNTLYLQMNSLKPEDTAMYYCAT  D-----------STGSH   RGQGTQVTVSS   Nb_6A4
              RFTISQDNAKNTVYLQMNSLKPEDTAMYYCNI  R--IGVGP-GGTCSIYAPY WGEGTQVTVSS   Nb_10C4
              RFTVSRDSSKNTVYLRMNSLKPEDTAIYYCAA  ASTWVPGFFPLFASQYNS  WGQGTQVTVSS   Nb_13B6
              RFTISRNNAQNTVYLQMNSLKPEDTATYSCAA  VSCAGAWFANRALRESAFTY WGPGTQVTVSS  Nb_1A4
              RFTISRDNAKNTVYLQMNSLKPEDTAVYYCNA  KNFFSASGYFL------Y  WGKGTQVTVSS   Nb_2B6
              RFTISRDNAKNTLYLQMNNLRPEDTAIYYCQL  GQ-WAGVGAAS------S  RGQGTQVTVSS   Nb_4A2
              RFTISRDNAKSTLYLQMDSLKSEDTAVYYCSK  GTGPFTDIRSTG-----S  PGKGTQVTVSS   Nb_1D4
              RFTISRDNAKNTLYLQMNSLKSEDTAVYYCTK  GLSPYRDLESSG-----S  RGQGTQVTVSS   Nb_9D3
```

FIG. 8
A
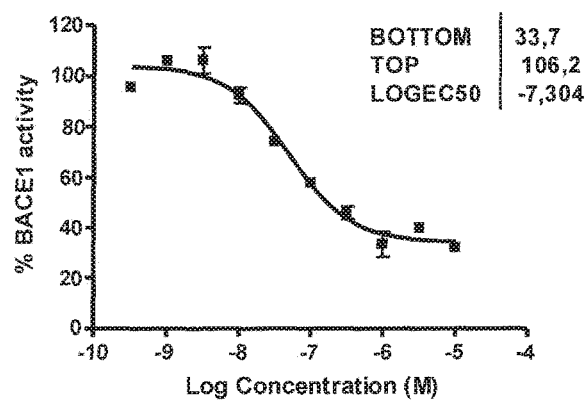
B
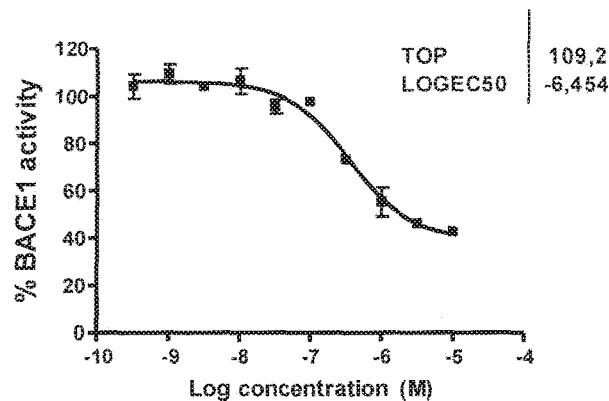
C
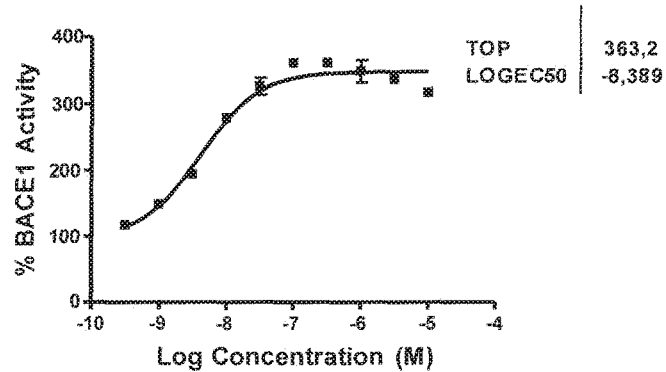

FIG. 11
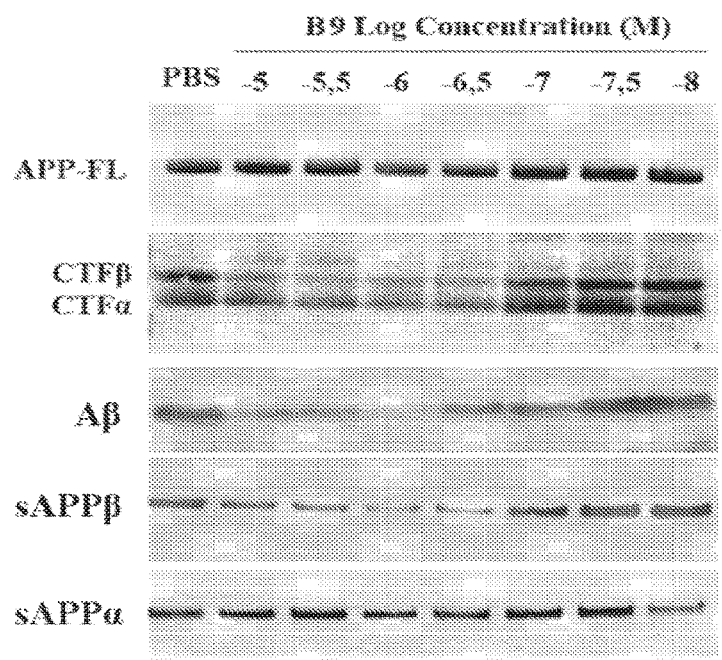
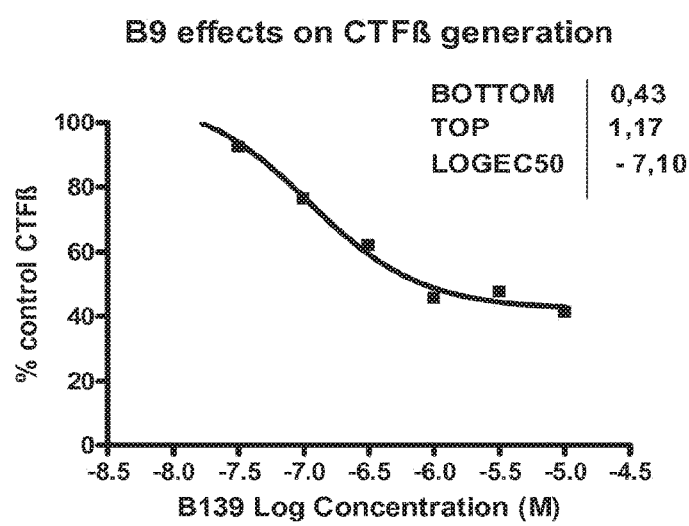
B9 effects on CTFß generation

SEQUENCE LISTING

<160> NUMBER OF SEQ ID NOS: 48

<210> SEQ ID NO 1
<211> LENGTH: 126
<212> TYPE: PRT
<213> ORGANISM: Camelus dromedarius

<400> SEQUENCE: 1

Asp Val Gln Leu Gln Glu Ser Gly Gly Gly Ser Val Gln Ala Gly Gly
1               5                   10                  15

Ser Leu Arg Leu Ser Cys Val Ala Ser Gly Trp Thr Tyr Ser Ser Asn
            20                  25                  30

Ser Leu Ser Met Ala Trp Phe Arg Gln Ala Pro Gly Lys Glu Arg Glu
        35                  40                  45

Gly Val Ala Thr Ile Thr Ser Tyr Val Gly Arg Thr Tyr Tyr Ala Asp
    50                  55                  60

Ser Val Lys Gly Arg Phe Thr Ile Ser Arg Asp His Ala Lys Ser Thr
65                  70                  75                  80

Val Tyr Leu Gln Ile Asp Ser Leu Lys Pro Glu Asp Thr Ala Thr Tyr
                85                  90                  95

Tyr Cys Ala Ala Glu Tyr Leu Gly Gly Ser Phe Leu Ser Thr Gly Ala
            100                 105                 110

Tyr Lys Tyr Trp Gly Gln Gly Thr Gln Val Thr Val Ser Ser
        115                 120                 125

<210> SEQ ID NO 2
<211> LENGTH: 127
<212> TYPE: PRT
<213> ORGANISM: Camelus dromedarius

<400> SEQUENCE: 2

Asp Val Gln Leu Gln Glu Ser Gly Gly Gly Ser Val Gln Ala Gly Gly
1               5                   10                  15

Ser Leu Arg Leu Ser Cys Ala Val Ser Gly Phe Ser Tyr Ser Pro Tyr
            20                  25                  30

Tyr Met Gly Trp Phe Arg Gln Ala Pro Gly Lys Glu Arg Glu Gly Val
        35                  40                  45

Ala Ala Ile Arg Lys Gly Ile Gly Thr Thr Tyr Ala Asp Ser Val
    50                  55                  60

Lys Gly Arg Phe Thr Phe Ser Gln Asp Asp Ala Lys Asn Thr Met Tyr
65                  70                  75                  80

Leu Gln Met Asn Ser Leu Lys Pro Glu Asp Thr Ala Ile Tyr Phe Cys
                85                  90                  95

Ala Val Gly His Tyr Arg Ala Tyr Ala Thr Thr Ser Phe Asp Pro Arg
            100                 105                 110

Arg Tyr Asp Tyr Trp Gly Gln Gly Thr Gln Val Thr Val Ser Ser
        115                 120                 125

<210> SEQ ID NO 3
<211> LENGTH: 125
<212> TYPE: PRT
<213> ORGANISM: Camelus dromedarius

<400> SEQUENCE: 3

Asp Val Gln Leu Gln Glu Ser Gly Gly Gly Ser Val Gln Ala Gly Gly
1               5                   10                  15

Ser Leu Arg Leu Ser Cys Ala Val Ser Gly Tyr Thr Tyr Asn Ile Tyr
            20                  25                  30

```
Thr Met Ala Trp Phe Arg Gln Ala Pro Gly Lys Glu Arg Glu Gly Val
            35                  40                  45

Ala Gly Ile Tyr Ser Pro Gly Thr Thr Tyr Tyr Ala Asp Ser Val
 50                  55                  60

Lys Gly Arg Phe Thr Ile Ser Gln Asp Asn Ala Lys Asn Thr Val Tyr
 65                  70                  75                  80

Leu Gln Met Asn Ser Leu Ala Pro Glu Asp Thr Ala Ile Tyr Tyr Cys
                 85                  90                  95

Ala Ala Arg Gly Gly Leu Leu Ser Arg Val Leu Lys Glu Ala Gly Tyr
            100                 105                 110

Asn Ala Trp Gly Gln Gly Thr Gln Val Thr Val Ser Ser
        115                 120                 125

<210> SEQ ID NO 4
<211> LENGTH: 125
<212> TYPE: PRT
<213> ORGANISM: Camelus dromedarius

<400> SEQUENCE: 4

Asp Val Gln Leu Gln Glu Ser Gly Gly Gly Ser Val Gln Ala Gly Gly
 1               5                  10                  15

Ser Leu Arg Leu Ser Cys Ala Ala Ser Gly Tyr Thr Phe Thr Lys Tyr
             20                  25                  30

Pro Met Gly Trp Phe Arg Gln Ala Pro Gly Lys Cys Glu Leu Val
            35                  40                  45

Ser Ser Ile Ile Ser Gly Gly Val Thr Thr Tyr Ala Ser Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Gln Tyr Pro Tyr Ser Ser Ser Trp Pro Arg Cys Pro Phe Arg Ile
            100                 105                 110

Gly Tyr Trp Gly Gln Gly Thr Gln Val Thr Val Ser Ser
        115                 120                 125

<210> SEQ ID NO 5
<211> LENGTH: 123
<212> TYPE: PRT
<213> ORGANISM: Camelus dromedarius

<400> SEQUENCE: 5

Asp Val Gln Leu Gln Glu Ser Gly Gly Gly Ser Val Gln Ala Gly Gly
 1               5                  10                  15

Ser Leu Arg Leu Ser Cys Ala Arg Ser Gly Gly Thr Val Ser Ile Pro
             20                  25                  30

Tyr Met Ala Trp Phe Arg Gln Gly Pro Gly Lys Glu Arg Glu Gly Val
            35                  40                  45

Ala Ala Ile Tyr Asp Gly Arg Ala Lys Thr Tyr Ala Gly Ser Leu Gln
 50                  55                  60

Gly Arg Phe Thr Ile Ser Gln Asp Asn Asp Lys Asn Thr Leu Tyr Leu
 65                  70                  75                  80

Gln Met Asn Ser Leu Lys Pro Asp Asp Thr Ala Val Tyr Tyr Cys Ala
                 85                  90                  95

Ala Gly Asn Gly Gly Gly Asn Trp Leu Arg Pro Ser Glu Tyr Asn Tyr
            100                 105                 110
```

Trp Gly Lys Gly Thr Gln Val Thr Val Ser Ser
        115                 120

<210> SEQ ID NO 6
<211> LENGTH: 121
<212> TYPE: PRT
<213> ORGANISM: Camelus dromedarius

<400> SEQUENCE: 6

Asp Val Gln Leu Gln Glu Ser Gly Gly Gly Ser Val Gln Ala Gly Gly
1               5                   10                  15

Ser Leu Arg Leu Ser Cys Ala Ala Ser Glu Tyr Thr Tyr Gly Tyr Cys
            20                  25                  30

Ser Met Gly Trp Tyr Arg Gln Ala Pro Gly Lys Glu Arg Glu Leu Val
        35                  40                  45

Ser Thr Ile Thr Ser Asp Gly Ser Thr Ser Tyr Val Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Lys Tyr Tyr Cys Tyr
                85                  90                  95

Thr Lys Thr Cys Ala Asn Lys Leu Gly Ala Lys Phe Ile Ser Trp Gly
            100                 105                 110

Gln Gly Thr Gln Val Thr Val Ser Ser
        115                 120

<210> SEQ ID NO 7
<211> LENGTH: 127
<212> TYPE: PRT
<213> ORGANISM: Camelus dromedarius

<400> SEQUENCE: 7

Asp Val Gln Leu Gln Glu Ser Gly Gly Gly Ser Val Gln Pro Gly Gly
1               5                   10                  15

Ser Leu Arg Leu Ser Cys Ala Ala Ser Gly Tyr Phe Tyr Ser Arg Trp
            20                  25                  30

Tyr Met Gly Trp Phe Arg Gln Ala Pro Gly Lys Glu Arg Glu Gly Val
        35                  40                  45

Ala Ala Ile Asn Ser Gly Gly Ser Ile Thr Ser Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Ala Leu Ser Arg Val Pro Gly Phe Phe Pro Leu Phe Pro Ser
            100                 105                 110

Gln Tyr Asn Tyr Trp Gly Gln Gly Thr Gln Val Thr Val Ser Ser
        115                 120                 125

<210> SEQ ID NO 8
<211> LENGTH: 129
<212> TYPE: PRT
<213> ORGANISM: Camelus dromedarius

<400> SEQUENCE: 8

Asp Val Gln Leu Gln Glu Ser Gly Gly Gly Ser Ala Gln Ala Gly Gly
1               5                   10                  15

-continued

```
Ser Leu Arg Leu Ser Cys Glu Val Ser Gly Tyr Thr Tyr Ser Gly Tyr
            20                  25                  30

Phe Met Gly Trp Phe Arg Gln Ala Pro Gly Glu Glu Arg Glu Gly Val
        35                  40                  45

Ala Ala Ile Asp Thr Asn Gly Arg Thr Trp Tyr Ala Asp Ser Val
    50                  55                  60

Lys Gly Arg Phe Thr Ile Ser His Asp Asn Ala Glu Ser Thr Val Tyr
65                  70                  75                  80

Leu Gln Met Asn Ser Leu Gln Pro Glu Asp Thr Ala Ile Tyr Phe Cys
                85                  90                  95

Ala Ala Arg Arg Pro Pro Gly Gly Ser Trp Tyr Pro Pro Leu Arg
            100                 105                 110

Lys Tyr Ser Tyr Asn Phe Trp Gly Gln Gly Thr Gln Val Thr Val Ser
            115                 120                 125

Ser
```

<210> SEQ ID NO 9
<211> LENGTH: 128
<212> TYPE: PRT
<213> ORGANISM: Camelus dromedarius

<400> SEQUENCE: 9

```
Asp Val Gln Leu Gln Glu Ser Gly Gly Gly Ser Val Gln Ala Gly Gly
1               5                   10                  15

Ser Leu Arg Leu Ser Cys Val Ala Ser Gly Phe Thr Tyr Arg Arg Tyr
            20                  25                  30

Phe Met Gly Trp Phe Arg Gln Ala Pro Gly Lys Glu Arg Glu Ala Val
        35                  40                  45

Ala Thr Met Phe Ser Cys Gly Gly Thr Thr Tyr Ala Asp Ser Val
    50                  55                  60

Lys Gly Arg Phe Thr Ala Thr Gln Asp Asn Ala Lys Asn Thr Val Tyr
65                  70                  75                  80

Leu Gln Met Asn Asn Leu Lys Pro Glu Asp Thr Ala Ile Tyr Tyr Cys
                85                  90                  95

Ala Ala Ala Ser Gly Cys Trp Tyr Asp Gly Ser Pro Ala Ala Arg Ser
            100                 105                 110

Val Asp Val Ser Phe Trp Gly His Gly Thr Gln Val Thr Val Ser Ser
            115                 120                 125
```

<210> SEQ ID NO 10
<211> LENGTH: 129
<212> TYPE: PRT
<213> ORGANISM: Camelus dromedarius

<400> SEQUENCE: 10

```
Asp Val Gln Leu Gln Glu Ser Gly Gly Gly Ser Val Gln Ala Gly Gly
1               5                   10                  15

Ser Leu Arg Leu Ser Cys Ala Ser Gly Tyr Ser Tyr Ser Tyr Tyr
            20                  25                  30

Ile Gly Trp Phe Arg Gln Ala Pro Gly Lys Glu Arg Glu Gly Val Ala
        35                  40                  45

Ala Ile Ala Ile Val Asn Ser Gly Gly Arg Thr Tyr Tyr Ala Asp
    50                  55                  60

Ser Val Lys Gly Arg Phe Thr Ile Ser Gln Gly Asn Asp Lys Asn Thr
65                  70                  75                  80

Val Tyr Leu Gln Met Asn Ser Leu Lys Pro Glu Asp Thr Ala Ile Tyr
```

```
                    85                  90                  95

Tyr Cys Ala Ala Arg Ser Leu Ser Trp Tyr Ser His Pro Leu Leu Gln
                100                 105                 110

Pro Ser Gln Phe Asn Asn Trp Gly Gln Gly Thr Gln Val Thr Val Ser
            115                 120                 125

Ser

<210> SEQ ID NO 11
<211> LENGTH: 128
<212> TYPE: PRT
<213> ORGANISM: Camelus dromedarius

<400> SEQUENCE: 11

Asp Val Gln Leu Gln Glu Ser Gly Gly Gly Ser Val Gln Ala Glu Gly
1               5                   10                  15

Ser Leu Arg Leu Ser Cys Thr Ala Ser Gly Tyr Thr Tyr Ser Leu Met
            20                  25                  30

Gly Trp Phe Arg Gln Ala Pro Gly Lys Glu Arg Glu Gly Val Ala Val
        35                  40                  45

Ile Asn Ser Gly Val Gly Thr Thr Tyr Tyr Ala Asp Ser Val Lys Gly
    50                  55                  60

Arg Phe Thr Ile Ser Gln Asp Asn Ala Lys Ser Thr Val Tyr Leu Gln
65                  70                  75                  80

Met Asn Ser Leu Lys Pro Glu Asp Thr Ala Ile Tyr Tyr Cys Ala Ala
                85                  90                  95

Arg Arg Ser Trp Phe Thr Gly Met Thr Thr Thr Gln Ala Leu Asp Pro
                100                 105                 110

Asp Trp Phe Ser Tyr Trp Gly Gln Gly Thr Gln Val Thr Val Ser Ser
            115                 120                 125

<210> SEQ ID NO 12
<211> LENGTH: 125
<212> TYPE: PRT
<213> ORGANISM: Camelus dromedarius

<400> SEQUENCE: 12

Asp Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Ser Glu Met Asn
            20                  25                  30

Arg Phe Ala Trp Leu Arg Gln Ala Pro Gly Lys Asp Arg Glu Val Val
        35                  40                  45

Ala Val Ile Phe Pro Thr Ala Arg Gly Ala Lys Phe Tyr Ser Asp Ser
    50                  55                  60

Val Asn Gly Arg Phe Thr Ile Ser Gln Asp Thr Ala Lys Asn Thr Val
65                  70                  75                  80

Tyr Leu Gln Met Asn Ser Leu Glu Pro Glu Asp Thr Ala Met Tyr Phe
                85                  90                  95

Cys Ala Ala Ser Ala Asn Ala Met Thr Gly Phe Gln Pro Ser Gly Tyr
                100                 105                 110

Thr Tyr Trp Gly Gln Gly Thr Gln Val Thr Val Ser Ser
            115                 120                 125

<210> SEQ ID NO 13
<211> LENGTH: 129
<212> TYPE: PRT
<213> ORGANISM: Camelus dromedarius
```

<400> SEQUENCE: 13

Gln Val Gln Leu Gln Glu Ser Gly Gly Gly Thr Val Gln Ala Gly Gly
1               5                   10                  15

Ser Leu Arg Leu Ser Cys Ala Ala Ser Gly Tyr Thr Tyr Arg Ser Tyr
            20                  25                  30

Cys Met Gly Trp Phe Arg Gln Ala Pro Gly Lys Glu Arg Glu Glu Val
        35                  40                  45

Ala Ser Ile Asn Ser Asp Gln Gly Ser Thr Arg Tyr Ala Ala Ser Val
    50                  55                  60

Lys Gly Arg Phe Thr Ser Ser Gln Asp Asn Ala Asn Asn Thr Val Thr
65                  70                  75                  80

Val Tyr Leu Gln Met Asn Ser Leu Lys Pro Glu Asp Thr Ala Ile Tyr
                85                  90                  95

Tyr Cys Ala Ala Asn Asp Gly Cys Ala Tyr Arg Val Tyr Arg Gly Gly
            100                 105                 110

Ala Tyr Gly Tyr Asn Phe Trp Gly Gln Gly Thr Gln Val Thr Val Ser
        115                 120                 125

Ser

<210> SEQ ID NO 14
<211> LENGTH: 129
<212> TYPE: PRT
<213> ORGANISM: Camelus dromedarius

<400> SEQUENCE: 14

Asp Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ala Phe Ser Ser Tyr
            20                  25                  30

Tyr Met Gly Trp Phe Arg Gln Ala Pro Gly Arg Glu Arg Glu Glu Val
        35                  40                  45

Thr Gly Ile Thr Gln Ile Gly Gly Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Ile Tyr Tyr Cys
                85                  90                  95

Ala Lys Leu Arg Arg Pro Phe Tyr Tyr Pro Leu Leu Glu Arg Pro Ser
            100                 105                 110

Glu Gly Asp Phe Asp Tyr Trp Gly Gln Gly Thr Gln Val Thr Val Ser
        115                 120                 125

Ser

<210> SEQ ID NO 15
<211> LENGTH: 126
<212> TYPE: PRT
<213> ORGANISM: Camelus dromedarius

<400> SEQUENCE: 15

Gln Val Gln Leu Gln Glu Ser Gly Gly Gly Ser Val Gln Ala Gly Gly
1               5                   10                  15

Ser Leu Arg Leu Ser Cys Ala Ala Ser Glu Tyr Thr Asp Ser Thr Tyr
            20                  25                  30

Tyr Met Ala Trp Phe Arg Gln Ala Pro Gly Lys Glu Arg Gly Gly Val
        35                  40                  45

Ala Thr Leu Ala Ser Arg Tyr Asp Thr Thr Tyr Tyr Ala Asp Ser Val
            50                  55                  60

Lys Gly Arg Phe Thr Ile Ser Gln Asp Arg Ala Lys Asn Thr Val Tyr
 65                  70                  75                  80

Leu Gln Met Asn Ser Leu Lys Pro Glu Asp Thr Gly Ile Tyr Tyr Cys
                    85                  90                  95

Ala Ala Ser Pro Arg Arg Pro Gly Phe Phe Pro Leu Asp Pro Ser Gln
                100                 105                 110

Tyr Asn Tyr Trp Gly Gln Gly Thr Gln Val Thr Val Ser Ser
                115                 120                 125

<210> SEQ ID NO 16
<211> LENGTH: 127
<212> TYPE: PRT
<213> ORGANISM: Camelus dromedarius

<400> SEQUENCE: 16

Gln Val Gln Leu Gln Glu Ser Gly Gly Gly Ser Val Gln Ala Gly Gly
  1               5                  10                  15

Ser Leu Arg Leu Ser Cys Ala Ala Ser Arg Asp Ile Leu Thr Leu Tyr
                 20                  25                  30

Tyr Met Gly Trp Phe Arg Gln Ala Pro Gly Lys Glu Arg Glu Gly Val
                 35                  40                  45

Ala Ala Ile Ser Ser Asp Ile Ile Phe Thr Ser Tyr Ala Asn Ser Val
            50                  55                  60

Lys Gly Arg Phe Thr Ile Ser Arg Asp Lys Asp Lys Asn Thr Val Tyr
 65                  70                  75                  80

Leu Gln Met Asn Ser Leu Lys Pro Glu Asp Thr Ala Ile Tyr Tyr Cys
                    85                  90                  95

Ala Ala Ala Ser Thr Trp Val Pro Gly Phe Phe Pro Leu Phe Ala Ser
                100                 105                 110

Gln Tyr Asn Ser Trp Gly Gln Gly Thr Gln Val Thr Val Ser Ser
                115                 120                 125

<210> SEQ ID NO 17
<211> LENGTH: 127
<212> TYPE: PRT
<213> ORGANISM: Camelus dromedarius

<400> SEQUENCE: 17

Gln Val Gln Leu Gln Glu Ser Gly Gly Gly Ser Val Gln Ala Gly Gly
  1               5                  10                  15

Ser Leu Arg Leu Ser Cys Ala Ala Ser Arg Asp Ile Leu Thr Leu Tyr
                 20                  25                  30

Tyr Met Gly Trp Phe Arg Gln Ala Pro Gly Lys Glu Arg Glu Gly Val
                 35                  40                  45

Ala Ala Ile Ser Ser Asp Ile Ile Phe Thr Ser Tyr Ala Asn Ser Val
            50                  55                  60

Lys Gly Arg Phe Thr Ile Ser Arg Asp Glu Asp Lys Asn Thr Val Tyr
 65                  70                  75                  80

Leu Gln Met Asn Ser Leu Lys Pro Glu Asp Thr Ala Ile Tyr Tyr Cys
                    85                  90                  95

Ala Ala Ala Ser Thr Trp Val Pro Gly Phe Phe Pro Leu Phe Ala Ser
                100                 105                 110

Gln Tyr Asn Ser Trp Gly Gln Gly Thr Gln Val Thr Val Ser Ser
                115                 120                 125

<210> SEQ ID NO 18
<211> LENGTH: 125
<212> TYPE: PRT
<213> ORGANISM: Camelus dromedarius

<400> SEQUENCE: 18

Gln Val Gln Leu Gln Glu Ser Gly Gly Gly Ser Val Gln Ala Gly Gly
1               5                   10                  15

Ser Leu Arg Leu Ser Cys Ala His Ser Asn Thr Tyr Pro Thr Tyr Met
            20                  25                  30

Gly Trp Phe Arg Gln Ala Pro Gly Lys Glu Arg Glu Gly Val Ala Ala
        35                  40                  45

Ile Tyr Thr Gly Asp Gly Thr Thr Tyr Tyr Gly Asp Ser Val Lys Gly
    50                  55                  60

Arg Phe Thr Ile Ser Gln Asp Asn Ala Lys Asn Thr Val Tyr Leu Gln
65                  70                  75                  80

Met Asn Ser Leu Lys Pro Glu Asp Thr Ala Ile Tyr Tyr Cys Ala Ala
                85                  90                  95

Ala Leu Ser Arg Val Pro Gly Phe Phe Pro Leu Phe Pro Ser Gln Tyr
            100                 105                 110

Asn Tyr Trp Gly Gln Gly Thr Gln Val Thr Val Ser Ser
        115                 120                 125

<210> SEQ ID NO 19
<211> LENGTH: 125
<212> TYPE: PRT
<213> ORGANISM: Camelus dromedarius

<400> SEQUENCE: 19

Gln Val Gln Leu Gln Glu Ser Gly Gly Gly Ser Val Gln Ala Gly Gly
1               5                   10                  15

Ser Leu Arg Leu Ser Cys Ala His Ser Asn Thr Tyr Pro Thr Tyr Met
            20                  25                  30

Gly Trp Phe Arg Gln Ala Pro Gly Lys Glu Arg Glu Gly Val Ala Ala
        35                  40                  45

Ile Tyr Thr Gly Asp Gly Thr Thr Tyr Tyr Gly Asp Ser Val Lys Gly
    50                  55                  60

Arg Phe Thr Ile Ser Gln Asp Asn Ala Lys Asn Thr Val Tyr Leu Gln
65                  70                  75                  80

Met Asn Ser Leu Lys Pro Glu Asp Thr Ala Ile Tyr Tyr Cys Ala Ala
                85                  90                  95

Ala Leu Ser Arg Val Pro Gly Phe Phe Pro Leu Phe Pro Ser Gln Tyr
            100                 105                 110

Asn Tyr Trp Gly Gln Gly Thr Gln Val Thr Val Ser Ser
        115                 120                 125

<210> SEQ ID NO 20
<211> LENGTH: 127
<212> TYPE: PRT
<213> ORGANISM: Camelus dromedarius

<400> SEQUENCE: 20

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Ser Ser Val Tyr
            20                  25                  30

```
Tyr Ile Ser Trp Phe Arg Gln Ala Pro Gly Lys Glu Arg Glu Gly Val
             35                  40                  45

Ala Ala Ile Asn Ser Gly Gly Gly Ile Thr Phe Tyr Ala Asp Ser Val
 50                      55                  60

Lys Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Ile Tyr Tyr Cys
                 85                  90                  95

Ala Ala Ala Leu Ser Arg Val Pro Gly Phe Phe Pro Leu Phe Pro Ser
             100                 105                 110

Gln Tyr Asn Tyr Trp Gly Gln Gly Thr Gln Val Thr Val Ser Ser
             115                 120                 125
```

<210> SEQ ID NO 21
<211> LENGTH: 115
<212> TYPE: PRT
<213> ORGANISM: Camelus dromedarius

<400> SEQUENCE: 21

```
Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Trp Met Tyr Trp Val Arg Gln Ala Pro Gly Lys Gly Leu Glu Trp Val
             35                  40                  45

Ser Gln Ile Asn Ser Gly Gly Gly Thr Thr Tyr Ser Thr Asp Ser Val
 50                      55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Asp Ser Thr Gly Ser His Arg Gly Gln Gly Thr Gln Val Thr
             100                 105                 110

Val Ser Ser
        115
```

<210> SEQ ID NO 22
<211> LENGTH: 124
<212> TYPE: PRT
<213> ORGANISM: Camelus dromedarius

<400> SEQUENCE: 22

```
Gln Val Gln Leu Gln Glu Ser Gly Gly Gly Ser Val Gln Ala Gly Gly
 1               5                  10                  15

Phe Leu Arg Leu Ser Cys Ala Ala Ser Gly Tyr Thr Tyr Ser Thr Cys
             20                  25                  30

Ser Met Ala Trp Tyr Arg Gln Ala Pro Gly Lys Glu Arg Glu Leu Val
             35                  40                  45

Ser Ser Ile Arg Asn Asp Gly Ser Thr Ala Tyr Ala Asp Ser Val Lys
         50                  55                  60

Gly Arg Phe Thr Ile Ser Gln Asp Asn Ala Lys Asn Thr Val Tyr Leu
 65                  70                  75                  80

Gln Met Asn Ser Leu Lys Pro Glu Asp Thr Ala Met Tyr Tyr Cys Asn
                 85                  90                  95

Ile Arg Ile Gly Val Gly Pro Gly Gly Thr Cys Ser Tyr Ala Pro
             100                 105                 110
```

```
Tyr Trp Gly Glu Gly Thr Gln Val Thr Val Ser Ser
        115                 120
```

<210> SEQ ID NO 23
<211> LENGTH: 127
<212> TYPE: PRT
<213> ORGANISM: Camelus dromedarius

<400> SEQUENCE: 23

```
Gln Val Gln Leu Gln Glu Ser Gly Gly Ser Val Gln Ala Gly Gly
1               5                   10                  15

Ser Leu Arg Leu Ser Cys Ala Ala Ser Gly Ile Ser Arg Ser Thr Tyr
            20                  25                  30

Phe Met Gly Trp Phe Arg Gln Ala Pro Gly Lys Glu Arg Glu Gly Val
        35                  40                  45

Ala Val Ile Asn Tyr Gly Thr Thr Thr Pro Tyr Tyr Pro Asp Ser Val
    50                  55                  60

Lys Gly Arg Phe Thr Val Ser Arg Asp Ser Ser Lys Asn Thr Val Tyr
65                  70                  75                  80

Leu Arg Met Asn Ser Leu Lys Pro Glu Asp Thr Ala Ile Tyr Tyr Cys
                85                  90                  95

Ala Ala Ala Ser Thr Trp Val Pro Gly Phe Phe Pro Leu Phe Ala Ser
            100                 105                 110

Gln Tyr Asn Ser Trp Gly Gln Gly Thr Gln Val Thr Val Ser Ser
        115                 120                 125
```

<210> SEQ ID NO 24
<211> LENGTH: 128
<212> TYPE: PRT
<213> ORGANISM: Camelus dromedarius

<400> SEQUENCE: 24

```
Gln Val Gln Leu Gln Glu Ser Gly Gly Ser Val Gln Ala Gly Gly
1               5                   10                  15

Ser Leu Arg Leu Ser Cys Ala Ala Ser Gly Ala Thr Ala Ser Asp Tyr
            20                  25                  30

Cys Met Gly Trp Phe Arg Gln Ala Pro Gly Lys Glu Arg Glu Gly Val
        35                  40                  45

Ala Ala Ile Ser Arg Gly Gly Met Thr Tyr His Val Asp Ser Val Arg
    50                  55                  60

Gly Arg Phe Thr Ile Ser Arg Asn Asn Ala Gln Asn Thr Val Tyr Leu
65                  70                  75                  80

Gln Met Asn Ser Leu Lys Pro Glu Asp Thr Ala Thr Tyr Ser Cys Ala
                85                  90                  95

Ala Val Ser Cys Ala Gly Ala Trp Phe Ala Asn Arg Ala Leu Arg Glu
            100                 105                 110

Ser Ala Phe Thr Tyr Trp Gly Pro Gly Thr Gln Val Thr Val Ser Ser
        115                 120                 125
```

<210> SEQ ID NO 25
<211> LENGTH: 120
<212> TYPE: PRT
<213> ORGANISM: Lama glama

<400> SEQUENCE: 25

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Asp Leu Arg
```

```
            20                  25                  30
Asp Met Gly Trp Tyr Arg Gln Val Pro Gly Lys Gln Arg Glu Leu Val
        35                  40                  45

Ala Ala Ile Thr Ser Gly Gly Thr Ser Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95

Ala Lys Asn Phe Phe Ser Ala Ser Gly Tyr Phe Leu Tyr Trp Gly Lys
            100                 105                 110

Gly Thr Gln Val Thr Val Ser Ser
            115                 120

<210> SEQ ID NO 26
<211> LENGTH: 121
<212> TYPE: PRT
<213> ORGANISM: Lama glama

<400> SEQUENCE: 26

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Glu Thr Gln
            20                  25                  30

Tyr Met Thr Trp Val Arg Gln Ala Pro Gly Lys Gly Pro Glu Tyr Val
        35                  40                  45

Ser Ser Ile Asn Ser Gly Gly Thr Ile Lys Tyr Ala Asn Ser Ser
    50                  55                  60

Val Lys Gly Arg Phe Thr Ile Ser Arg Asp Asn Ala Lys Asn Thr Leu
65                  70                  75                  80

Tyr Leu Gln Met Asn Asn Leu Arg Pro Glu Asp Thr Ala Ile Tyr Tyr
            85                  90                  95

Cys Gln Leu Gly Gln Trp Ala Gly Val Gly Ala Ala Ser Ser Arg Gly
            100                 105                 110

Gln Gly Thr Gln Val Thr Val Ser Ser
            115                 120

<210> SEQ ID NO 27
<211> LENGTH: 122
<212> TYPE: PRT
<213> ORGANISM: Lama glama

<400> SEQUENCE: 27

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Tyr Trp Val Arg Gln Ala Pro Gly Lys Gly Leu Glu Trp Val
        35                  40                  45

Ser Ala Ile Ser Thr Glu Gly Gly Ser Thr Arg Tyr Ala Gly Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Lys Ser Glu Asp Thr Ala Val Tyr Tyr Cys
            85                  90                  95

Ser Lys Gly Thr Gly Pro Phe Thr Asp Ile Arg Ser Thr Gly Ser Arg
```

Gly Lys Gly Thr Gln Val Thr Val Ser Ser
        115                 120

<210> SEQ ID NO 28
<211> LENGTH: 122
<212> TYPE: PRT
<213> ORGANISM: Lama glama

<400> SEQUENCE: 28

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Phe Arg Gln Ala Pro Gly Lys Gly Leu Glu Arg Val
        35                  40                  45

Ser Ala Ile Asn Phe Gly Gly Asp Val Thr Tyr Tyr Thr Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Thr Lys Gly Leu Ser Pro Tyr Arg Asp Leu Glu Ser Ser Gly Ser Arg
            100                 105                 110

Gly Gln Gly Thr Gln Val Thr Val Ser Ser
        115                 120

<210> SEQ ID NO 29
<211> LENGTH: 10
<212> TYPE: PRT
<213> ORGANISM: Camelus dromedarius

<400> SEQUENCE: 29

Glu Tyr Thr Tyr Gly Tyr Cys Ser Met Gly
1               5                   10

<210> SEQ ID NO 30
<211> LENGTH: 16
<212> TYPE: PRT
<213> ORGANISM: Camelus dromedarius

<400> SEQUENCE: 30

Thr Ile Thr Ser Asp Gly Ser Thr Ser Tyr Val Asp Ser Val Lys Gly
1               5                   10                  15

<210> SEQ ID NO 31
<211> LENGTH: 13
<212> TYPE: PRT
<213> ORGANISM: Camelus dromedarius

<400> SEQUENCE: 31

Lys Thr Cys Ala Asn Lys Leu Gly Ala Lys Phe Ile Ser
1               5                   10

<210> SEQ ID NO 32
<211> LENGTH: 10
<212> TYPE: PRT
<213> ORGANISM: Camelus dromedarius

<400> SEQUENCE: 32

Gly Tyr Thr Tyr Ser Thr Cys Ser Met Ala

```
<210> SEQ ID NO 33
<211> LENGTH: 16
<212> TYPE: PRT
<213> ORGANISM: Camelus dromedarius

<400> SEQUENCE: 33

Ser Ile Arg Asn Asp Gly Ser Thr Ala Tyr Ala Asp Ser Val Lys Gly
1               5                   10                  15

<210> SEQ ID NO 34
<211> LENGTH: 16
<212> TYPE: PRT
<213> ORGANISM: Camelus dromedarius

<400> SEQUENCE: 34

Arg Ile Gly Val Gly Pro Gly Gly Thr Cys Ser Ile Tyr Ala Pro Tyr
1               5                   10                  15

<210> SEQ ID NO 35
<211> LENGTH: 10
<212> TYPE: PRT
<213> ORGANISM: Lama glama

<400> SEQUENCE: 35

Gly Phe Thr Phe Glu Thr Gln Tyr Met Thr
1               5                   10

<210> SEQ ID NO 36
<211> LENGTH: 18
<212> TYPE: PRT
<213> ORGANISM: Lama glama

<400> SEQUENCE: 36

Ser Ile Asn Ser Gly Gly Thr Ile Lys Tyr Tyr Ala Asn Ser Ser Val
1               5                   10                  15

Lys Gly

<210> SEQ ID NO 37
<211> LENGTH: 11
<212> TYPE: PRT
<213> ORGANISM: Lama glama

<400> SEQUENCE: 37

Gly Gln Trp Ala Gly Val Gly Ala Ala Ser Ser
1               5                   10

<210> SEQ ID NO 38
<211> LENGTH: 115
<212> TYPE: PRT
<213> ORGANISM: Camelus dromedarius

<400> SEQUENCE: 38

Asp Val Gln Leu Gln Glu Ser Gly Gly Gly Leu Val Gln Pro Gly Gly
1               5                   10                  15

Ser Leu Arg Leu Ser Cys Ala Ala Ser Glu Phe Thr Phe Gly Ser Tyr
            20                  25                  30

Trp Met Tyr Trp Val Arg Gln Ala Pro Gly Lys Gly Leu Glu Trp Val
        35                  40                  45

Ala Gln Ile Asn Ala Arg Gly Ser Thr Ile Tyr Tyr Val Asp Ser Val
    50                  55                  60
```

```
Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Thr Asp Ser Arg Gly Thr His Lys Gly Gln Gly Thr Gln Val Thr
            100                 105                 110

Val Ser Ser
        115

<210> SEQ ID NO 39
<211> LENGTH: 115
<212> TYPE: PRT
<213> ORGANISM: Camelus dromedarius

<400> SEQUENCE: 39

Asp Val Gln Leu Gln Glu Ser Gly Gly Gly Leu Val Arg Pro Gly Gly
 1               5                  10                  15

Ser Leu Arg Leu Ser Cys Ala Ala Ser Gly Phe Thr Phe Ala Asn Tyr
            20                  25                  30

Trp Leu Tyr Trp Val Arg Asp Ala Pro Gly Lys Gly Ile Glu Trp Val
        35                  40                  45

Ser Gln Ile Gly Pro Ser Gly Arg Ser Thr Tyr Tyr Ala Asp Ala Val
    50                  55                  60

Lys Gly Arg Phe Thr Ile Ser Arg Asp Asn Ala Lys Lys Thr Leu Tyr
 65                  70                  75                  80

Leu Gln Met Asn Ser Leu Lys Pro Glu Asp Ser Ala Val Tyr Tyr Cys
                 85                  90                  95

Ala Thr Ser Ser Gly Gly Asn Glu Arg Gly Gln Gly Thr Gln Val Thr
            100                 105                 110

Val Ser Ser
        115

<210> SEQ ID NO 40
<211> LENGTH: 115
<212> TYPE: PRT
<213> ORGANISM: Camelus dromedarius

<400> SEQUENCE: 40

Asp Val Gln Leu Gln Glu Ser Gly Gly Gly Leu Val Gln Pro Gly Gly
 1               5                  10                  15

Ser Leu Arg Leu Ser Cys Ala Ala Ser Gly Phe Ala Phe Ser Ser Tyr
            20                  25                  30

Trp Met Tyr Trp Val Arg Gln Ala Pro Gly Lys Gly Leu Glu Trp Val
        35                  40                  45

Ser Gln Val Asn Ser Asp Gly Ser Thr Tyr Tyr Val Asp Ser Val
    50                  55                  60

Lys Gly Arg Phe Thr Ile Ser Arg Asp Asn Ala Lys Asn Thr Leu Tyr
 65                  70                  75                  80

Leu His Met Asn Ser Leu Lys Pro Glu Asp Thr Ala Val Tyr Tyr Cys
                 85                  90                  95

Ala Thr Asp Ser Ser Gly Arg Tyr Arg Gly Gln Gly Thr Gln Val Thr
            100                 105                 110

Val Ser Ser
        115

<210> SEQ ID NO 41
<211> LENGTH: 115
```

<212> TYPE: PRT
<213> ORGANISM: Camelus dromedarius

<400> SEQUENCE: 41

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ser Gln Ile Asn Ser Ser Gly Gly Thr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Gly Ser Ala Gly Gln Gly Lys Gly Gln Gly Thr Gln Val Thr
            100                 105                 110

Val Ser Ser
        115

<210> SEQ ID NO 42
<211> LENGTH: 115
<212> TYPE: PRT
<213> ORGANISM: Camelus dromedarius

<400> SEQUENCE: 42

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Gln Ile Asp Gly Gly Gly Arg Lys Thr Tyr Tyr Ala Asp Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Asp Ser Ala Gly Ser His Arg Gly Gln Gly Thr Gln Val Thr
            100                 105                 110

Val Ser Ser
        115

<210> SEQ ID NO 43
<211> LENGTH: 115
<212> TYPE: PRT
<213> ORGANISM: Camelus dromedarius

<400> SEQUENCE: 43

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Pro Phe Ser Val Tyr
            20                  25                  30

Trp Met Tyr Trp Val Arg Gln Ala Pro Gly Lys Gly Leu Glu Trp Val
        35                  40                  45

Ser Gln Ile Asp Ser Gly Gly Tyr Thr Thr Tyr Tyr Thr Asp Ser Val

```
            50                  55                  60
Lys Gly Arg Phe Ser Ala Ser Arg Asp Asn Ser Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Thr Asp Ser Ile Gly Ser Asn Lys Gly Gln Gly Thr Gln Val Thr
            100                 105                 110

Val Ser Ser
        115

<210> SEQ ID NO 44
<211> LENGTH: 23
<212> TYPE: DNA
<213> ORGANISM: Artificial Sequence
<220> FEATURE:
<223> OTHER INFORMATION: Primer CALL001

<400> SEQUENCE: 44
gtcctggctg ctcttctaca agg                                         23

<210> SEQ ID NO 45
<211> LENGTH: 23
<212> TYPE: DNA
<213> ORGANISM: Artificial Sequence
<220> FEATURE:
<223> OTHER INFORMATION: Primer CALL002

<400> SEQUENCE: 45
ggtacgtgct gttgaactgt tcc                                         23

<210> SEQ ID NO 46
<211> LENGTH: 29
<212> TYPE: DNA
<213> ORGANISM: Artificial Sequence
<220> FEATURE:
<223> OTHER INFORMATION: AE6

<400> SEQUENCE: 46
gatgtgcagc tgcaggagtc tggaggagg                                   29

<210> SEQ ID NO 47
<211> LENGTH: 35
<212> TYPE: DNA
<213> ORGANISM: Artificial Sequence
<220> FEATURE:
<223> OTHER INFORMATION: Primer FR4FOR

<400> SEQUENCE: 47
ggactagtgc ggccgctgca gacggtgacc tgggt                            35

<210> SEQ ID NO 48
<211> LENGTH: 15
<212> TYPE: PRT
<213> ORGANISM: Artificial Sequence
<220> FEATURE:
<223> OTHER INFORMATION: FRET peptide substrate

<400> SEQUENCE: 48

Ser Glu Val Asn Leu Asp Ala Glu Phe Arg Lys Arg Arg Arg Arg
 1               5                  10                  15
```

SINGLE DOMAIN ANTIBODIES CAPABLE OF MODULATING BACE ACTIVITY

CROSS-REFERENCE TO RELATED APPLICATIONS

The present application is a continuation of U.S. patent application Ser. No. 14/023,586, filed Sep. 11, 2013 (Allowed), which is a continuation of U.S. patent application Ser. No. 12/736,389, filed Dec. 27, 2010, issued on Oct. 29, 2013 as U.S. Pat. No. 8,568,717, which application is a national stage filing under 35 U.S.C. § 371 of International Application No. PCT/EP2009/053985, filed on Apr. 3, 2009, and published in English on Oct. 8, 2009 as WO 2009/121948 A2, which application claims the benefit of U.S. Patent Application Ser. No. 61/041,965, filed Apr. 3, 2008.

TECHNICAL FIELD

Described are single domain antibodies with a specificity for BACE1. More specifically, described are single variable-domain antibodies derived from camelids that bind to BACE1 and are capable of inhibiting the activity of BACE1. The antibodies can be used for research and medical applications. Specific applications include the use of BACE1-specific antibodies for the treatment of Alzheimer's disease.

BACKGROUND

Alzheimer's disease ("AD") is a devastating neurodegenerative disease that affects millions of elderly patients worldwide and is the most common cause of nursing home admittance. AD is clinically characterized by progressive loss of memory, orientation, cognitive function, judgment and emotional stability. With increasing age, the risk of developing AD increases exponentially, so that by age 85, some 20% to 40% of the population is affected. Memory and cognitive function deteriorate rapidly within the first five years after diagnosis of mild to moderate impairment, and death due to disease complications is an inevitable outcome. Definitive diagnosis of AD can only be made post-mortem, based on histopathological examination of brain tissue from the patient. Two histological hallmarks of AD are the occurrence of neurofibrillar tangles of hyperphosphorylated tau protein and of proteinaceous amyloid plaques, both within the cerebral cortex of AD patients. The amyloid plaques are composed mainly of a peptide of 37 to 43 amino acids designated "beta-amyloid," also referred to as "beta amyloid," "amyloid beta," "Aβ" or "Abeta." It is now clear that the Abeta peptide is derived from a type 1 integral membrane protein, termed "beta amyloid precursor protein" (also referred to as "APP") through two sequential proteolytic events. First, the APP is hydrolyzed at a site N-terminal of the transmembrane alpha helix by a specific proteolytic enzyme referred to as "beta-secretase" (the membrane-bound protease BACE1). The soluble N-terminal product of this cleavage event diffuses away from the membrane, leaving behind the membrane-associated C-terminal cleavage product, referred to as "C99." The protein C99 is then further hydrolyzed within the transmembrane alpha helix by a specific proteolytic enzyme referred to as "gamma-secretase." This second cleavage event liberates the Abeta peptide and leaves a membrane-associated "stub." The Abeta peptide thus generated is secreted from the cell into the extracellular matrix where it eventually forms the amyloid plaques associated with AD.

Despite intensive research during the last 100 years, prognosis of AD patients now is still quite the same as that of patients a century ago, since there is still no real cure available. There are two types of drugs approved by the U.S. Food and Drug Administration and used in clinics today to treat AD: Acetylcholinesterase (AchE) inhibitors and Memantine. There is ample evidence in the art that the amyloid beta peptide, the main component of the amyloid plaques that are specific to the AD etiology, has a key role in the development of AD disease. Therefore, one of the most favorite strategies to lower Aβ is to diminish its production by γ- and β-secretase inhibitors. One strategy was the development of gamma-secretase inhibitors; however, such inhibitors often result in serious side effects since gamma-secretase is involved in the proteolytic processing of at least 30 proteins.

Yet another attractive strategy is the development of BACE1 inhibitors. BACE1 is produced as a prepropeptide. The 21-amino acid signal peptide translocates the protease into the ER where the signal peptide is cleaved off and from where BACE1 is then directed to the cell surface. After its passage through the trans-Golgi network (TGN), part of BACE1 is targeted to the cell surface from where it is internalized into early endosomal compartments. BACE1 then either enters a direct recycling route to the cell surface or is targeted to late endosomal vesicles destined for the lysosomes or for the TGN. At the TGN, it might be retransported to the cell membrane. Given its long half-life and fast recycling rate, mature BACE1 may cycle multiple times between cell surface, endosomal system and TGN during the course of its lifespan. BACE1 inhibitory antibodies are described in US20060034848.

SUMMARY OF THE DISCLOSURE

Herein, we sought to develop alternative inhibitors of the activity of BACE1 through the generation of single chain antibodies with a specificity for BACE1. In the resulting collection of binders of BACE1, we identified inhibitors of BACE1. In particular, these BACE1-specific camelid antibodies capable of inhibiting BACE1 activity can be used for the treatment of Alzheimer's disease.

BRIEF DESCRIPTION OF THE DRAWINGS

FIG. 1: Amino acid sequence alignment of the variable domain of the BACE1-specific dromedary HCAbs (listed, in order, Nb_B1, Nb_B2, Nb_B3, Nb_B5, Nb_B8, Nb_B9, Nb_B10, Nb_B11, Nb_B12, Nb_B15, Nb_B16, Nb_B21, Nb_B25, and Nb_B26, corresponding with SEQ ID NOS: 1-14, respectively; and Nb_B4, Nb_B6, Nb_B7, Nb_B13, Nb_B14 and Nb_B24, corresponding with SEQ ID NOS: 38-43, respectively). $V_H H$ hallmark residues ($F/Y_{37}$, $E/Q_{44}$, $R_{45}$ and $G_{47}$) are indicated in bold, whereas residues characteristic for a VH-motif ($L_{11}$, $V_{37}$, $G_{44}$, $L_{45}$ and $W_{47}$) are labeled in italics. Cysteine residues other than the canonical $C_{22}$ and $C_{92}$ are underlined. Numbering and grouping of residues into either framework or CDR regions are as defined by Kabat (Kabat et al., 1991).

FIG. 3: Effect of Nb_B26 and Nb_B9 on APP processing in cells. Panel A: Schematic representation of the cDNA construct used to express $V_HH$s into mammalian cells. The construct consists of the $V_HH$ cDNA, fused at its C-terminus to the signal peptide of BACE1, to ensure ER translocation, and at its C-terminus it is fused to a myc-epitope tag. Panel B: Nb_B9, but not Nb_B26, adversely affects β-site APP processing upon transient overexpression. COS-B1 cells, stably expressing low levels of BACE1, were co-transfected with $APP_{Sw}$ and either Nb_B26 or Nb_B9. Control cells were either transfected with empty vector or with $APP_{Sw}$ alone. Two days after transfection, cells were lysed and total protein extracts were analyzed by Western blotting using anti-myc, anti-BACE1 (ProSci) and B63.1, to detect $V_HH$s, BACE1 and APP full length and CTFs (C83 and C99), respectively. One representative experiment is shown. Panel C: Western blots as the one shown in Panel C were probed with GARIR800, an infrared-coupled secondary antibody, and then scanned on an ODYSSEY® scanner. The signal intensity of the APP CTFs was quantified using the ODYSSEY® Application Software v1.2.15 (LI-COR). The ratio of β-CTF to total CTFs (mean±SEM, n=8 to 10), normalized to the ratio of non-transfected cells (set as 1), shows that Nb_B9 could consistently decrease activity by about 30% (t-test, p<0.001), whereas Nb_B26 had no impact on APP processing.

FIG. 4: $V_HH$ Nb_B9 inhibits β-secretase cleavage of APP by adding to the medium of cultured cells. Neuroblastoma cells SH-SY5Y/APPwt were treated with 3 µM NANOBODIES® for 24 hours, sAPPα and sAPPβ from conditioned medium were analyzed by Western blot. Cells treated with NANOBODY® B9 (SEQ ID NO:6) showed a significant decrease in sAPPβ producing.

FIG. 5: Amino acid sequence alignment of BACE1-specific $V_HH$s isolated from dromedary and llama $V_HH$ libraries (SEQ ID NOS:6, and 15-28). Numbering and grouping of residues into either framework or CDR regions are as defined by Kabat (Kabat et al., 1991).

FIG. 8: Dose-response curve of NANOBODIES® 10C4 (Panel A), 4A2 (Panel B), and B9 (Panel C) on BACE1 cleavage activity in FRET assay using a small peptide substrate. Nb_10C4 and Nb_4A2 significantly inhibit BACE1 activity. Nb_B9 significantly increases BACE1 activity.

FIG. 11: Dose response curve of $V_HH$s Nb_B9 (SEQ ID NO:6) inhibiting BACE1 in primary cultured mouse neurons established by metabolic labeling assays after a 6-hour treatment. Primary cultured neurons from wild-type mice were transduced with APPwt by Semliki Forest Virus (SFV), and treated with purified $V_HH$ B9 by adding to the medium serial dilutions ($V_HH$ B9 was first dissolved and diluted in PBS). Neuron cultures were metabolic labeled for 6 hours, APP-FL and CTFβ from cell extracts were analyzed by phosphorimaging, while sAPPβ, Aβ and sAPPα from conditioned medium were analyzed by Western blot.

DETAILED DESCRIPTION

Figure 2:
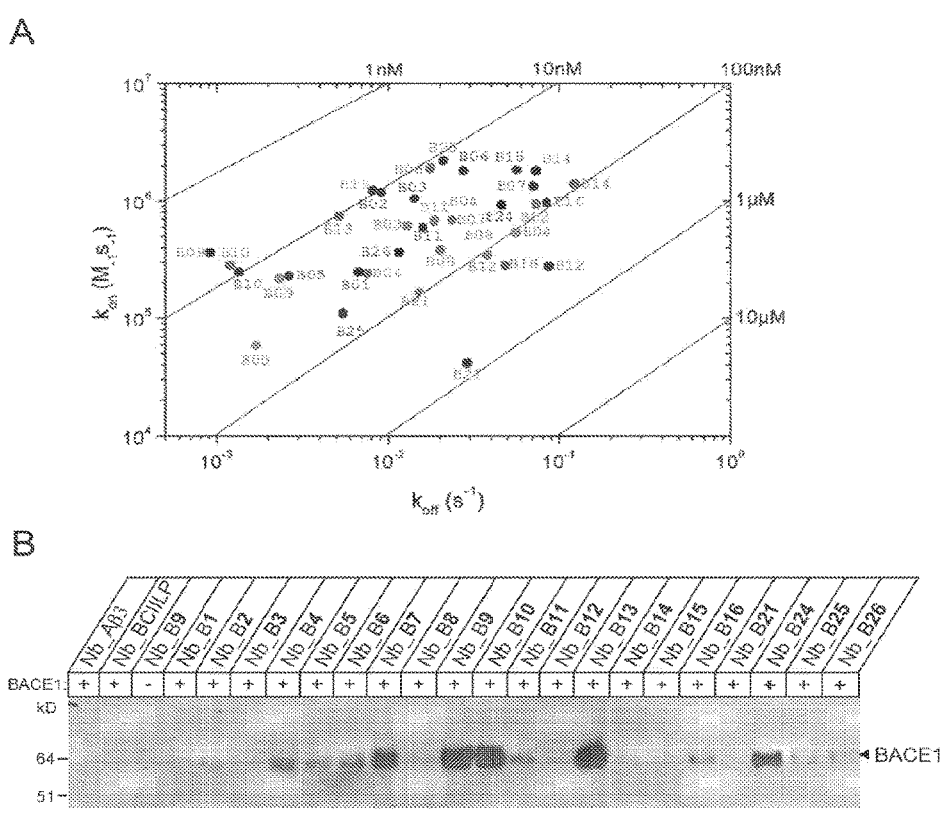
FIG. 2: Capacity of the different BACE1 binders to recognize their antigen. Panel A: A RaPID plot representing the kinetic rate values $k_{on}$ ($M^{-1}$ $s^{-1}$) and $k_{off}$ ($s^{-1}$) for the NANOBODY®-immunogen interactions as determined by surface plasmon resonance (BIAcore). The ratio of $k_{off}$ to $k_{on}$ gives the dissociation constant or $K_D$. Kinetic constants were measured at pH 7.0 (black spots) and pH 5.0 (gray spots). The majority of the BACE1 binders has $K_D$ values between 10 nM and 100 nM at both pH conditions. Panel B: Capacity of the different BACE1 binders to pull down BACE1 from cell lysates. Lysates of BACE1-transfected COS cells were incubated with equal amounts (2 µg) of the various recombinant his-tagged anti-BACE1 NANOBODIES.® Following pull down of the NANOBODIES®, samples were subjected to SDS-PAGE and analyzed by Western blotting using anti-BACE1 (ProSci). Nb_BCIILP and Nb_Aβ3, raised against beta-lactamase BCII 569/H (Conrath et al., 2001a) and Aβ peptide, respectively, were used as negative controls. Only part of the NANOBODIES®, raised against non-glycosylated BACE1 ectodomain, are able to efficiently capture glycosylated BACE1 from COS cell lysates.

Described are BACE1 single variable-domain antibodies that can be used in research and medical applications. More specifically, described is the detection of BACE1 overexpression and to the treatment of Alzheimer's disease using BACE1 single domain antibodies. As used herein, the antibodies are devoid of any light chain but comprise at least one heavy chain antibody. In a particular embodiment, the variable domain of a heavy chain antibody is derived from camelids. Such a variable domain heavy chain antibody is herein designated as a NANOBODY® or a $V_HH$ antibody. NANOBODY®, NANOBODIES®, and NANOCLONE® are trademarks of Ablynx NV (Belgium).

Thus, in a first embodiment, provided is a single variable-domain antibody, devoid of a light chain, specifically binding to BACE1. In a particular embodiment, the single domain antibody is derived from camelids. In the family of "camelids," immunoglobulins devoid of light polypeptide chains are found. "Camelids" comprise old-world camelids (*Camelus bactrianus* and *Camelus dromaderius*) and new world camelids (for example, *Lama paccos, Lama glama* and *Lama vicugna*).

In another embodiment, provided is a single domain antibody derived from camelids, which amino acid sequence comprises SEQ ID NOS:1-28. The amino acid sequences of the dromedary/llama NANOBODIES® (also designated as $V_HH$ antibodies) are depicted in FIGS. 1 and 5. NANOBODY® B1 (Nb_B1) corresponds with SEQ ID NO:1, NANOBODY® B2 (Nb_B2) corresponds with SEQ ID NO:2, NANOBODY® B3 (Nb_B3) corresponds with SEQ ID NO:3, NANOBODY® B5 (Nb_B5) corresponds with SEQ ID NO:4, NANOBODY® B8 (Nb_B8) corresponds with SEQ ID NO:5, NANOBODY® B9 (Nb_B9) corresponds with SEQ ID NO:6, NANOBODY® B10 (Nb_B10)

corresponds with SEQ ID NO:7, NANOBODY® 11 (Nb_B11) corresponds with SEQ ID NO:8, NANOBODY® 12 (Nb_B12) corresponds with SEQ ID NO:9, NANOBODY® 15 (Nb_B15) corresponds with SEQ ID NO:10, NANOBODY® 16 (Nb_B16) corresponds with SEQ ID NO:11, NANOBODY® 21 (Nb_B21) corresponds with SEQ ID NO:12, NANOBODY® 25 (Nb_B25) corresponds with SEQ ID NO:13, NANOBODY® 26 (Nb_B26) corresponds with SEQ ID NO:14, NANOBODY® 1B3 (Nb_1B3) corresponds with SEQ ID NO:15, NANOBODY® 10C2 (Nb_10C2) corresponds with SEQ ID NO:16, NANOBODY® 12B6 (Nb_12B6) corresponds with SEQ ID NO:17, NANOBODY® 10B5 (Nb_10B5) corresponds with SEQ ID NO:18, NANOBODY® 13A5 (Nb_13A5) corresponds with SEQ ID NO:19, NANOBODY® 2C6 (Nb2C6) corresponds with SEQ ID NO:20, NANOBODY® 6A4 (Nb_6A4) corresponds with SEQ ID NO:21, NANOBODY® 10C4 (Nb_10C4) corresponds with SEQ ID NO:22, NANOBODY® 13B6 (Nb_13B6) corresponds with SEQ ID NO:23, NANOBODY® 1A4 (Nb_1A4) corresponds with SEQ ID NO:24, NANOBODY® 2B6 (Nb_2B6) corresponds with SEQ ID NO:25, NANOBODY® 4A2 (Nb_4A2) corresponds with SEQ ID NO:26, NANOBODY® 1D4 (Nb_1D4) corresponds with SEQ ID NO:27 and NANOBODY® 9D3 (Nb_9D3) corresponds with SEQ ID NO:28.

In yet another embodiment, the single domain antibody is capable of inhibiting the activity of BACE1. It is understood that "inhibition of the activity" is equivalent with the wording "down-regulating the activity." Generally, "inhibition" means that the activity of BACE1 is inhibited by at least 30%, at least 40%, at least 50%, at least 60%, at least 70%, at least 80%, at least 90%, at least 95% or even 96%, 97%, 98%, 99% or even 100%. Inhibition of BACE1 can be determined as mentioned herein further in the examples.

In yet another embodiment, the single domain antibody is capable of inhibiting the activity of BACE1 and it comprises at least one of the complementarity-determining regions (CDRs) with an amino acid sequence selected from the group comprising SEQ ID NOS:29-37.

In yet another embodiment, the single domain antibody is capable of preventing the uptake of pro-BACE1 and its amino acid sequence comprises SEQ ID NOS:6, 22 or 26.

It should be noted that the term "NANOBODY®" as used herein in its broadest sense is not limited to a specific biological source or to a specific method of preparation. For example, the NANOBODIES® hereof can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding a such humanized $V_HH$ domain; (4) by "camelization" of a naturally occurring VH domain from any animal species and, in particular, from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a NANOBODY® using techniques for nucleic acid synthesis known per se, followed by expression of the nucleic acid thus obtained; and/or (8) by any combination of one or more of the foregoing. One preferred class of NANOBODIES® corresponds to the $V_HH$ domains of naturally occurring heavy chain antibodies directed against BACE1. As further described herein, such $V_HH$ sequences can generally be generated or obtained by suitably immunizing a species of camelid with BACE1 (i.e., so as to raise an immune response and/or heavy chain antibodies directed against BACE1), by obtaining a suitable biological sample from the camelid (such as a blood sample, serum sample or sample of B-cells), and by generating $V_HH$ sequences directed against BACE1, starting from the sample, using any suitable technique known per se. Such techniques will be clear to the skilled person.

Alternatively, such naturally occurring $V_HH$ domains against BACE1 can be obtained from naive libraries of Camelid $V_HH$ sequences, for example, by screening such a library using BACE1 or at least one part, fragment, antigenic determinant or epitope thereof using one or more known screening techniques per se. Such libraries and techniques are, for example, described in WO9937681, WO0190190, WO03025020 and WO03035694. Alternatively, improved synthetic or semi-synthetic libraries derived from naive $V_HH$ libraries may be used, such as $V_HH$ libraries obtained from naive $V_HH$ libraries by techniques such as random mutagenesis and/or CDR shuffling, such as, for example, described in WO0043507. Yet another technique for obtaining $V_HH$ sequences directed against BACE1 involves suitably immunizing a transgenic mammal that is capable of expressing heavy chain antibodies (i.e., so as to raise an immune response and/or heavy chain antibodies directed against BACE1), obtaining a suitable biological sample from the transgenic mammal (such as a blood sample, serum sample or sample of B-cells), and then generating $V_HH$ sequences directed against BACE1 starting from the sample, using any suitable technique known per se. For example, for this purpose, the heavy chain antibody-expressing mice and the further methods and techniques described in WO02085945 and in WO04049794 can be used.

A particularly preferred class of NANOBODIES® hereof comprises NANOBODIES® with an amino acid sequence that corresponds to the amino acid sequence of a naturally occurring $V_HH$ domain, but that has been "humanized," i.e., by replacing one or more amino acid residues in the amino acid sequence of the naturally occurring $V_HH$ sequence (and, in particular, in the framework sequences) by one or more of the amino acid residues that occur at the corresponding position(s) in a VH domain from a conventional four-chain antibody from a human being. This can be performed in a manner known per se, which will be clear to the skilled person, for example, on the basis of the further description herein and the prior art on humanization referred to herein. Again, it should be noted that such humanized NANOBODIES® of the invention can be obtained in any suitable manner known per se (i.e., as indicated under points (1)-(8) above) and, thus, are not strictly limited to polypeptides that have been obtained using a polypeptide that comprises a naturally occurring $V_HH$ domain as a starting material.

Another particularly preferred class of NANOBODIES® of the invention comprises NANOBODIES® with an amino acid sequence that corresponds to the amino acid sequence of a naturally occurring VH domain, but that has been "camelized," i.e., by replacing one or more amino acid residues in the amino acid sequence of a naturally occurring VH domain from a conventional four-chain antibody by one or more of the amino acid residues that occur at the corresponding position(s) in a $V_HH$ domain of a heavy chain antibody. Such "camelizing" substitutions are preferably inserted at amino acid positions that form and/or are present at the VH-VL interface, and/or at the so-called Camelidae hallmark residues, as defined herein (see, for example, WO9404678). Preferably, the VH sequence that is used as a starting material or starting point for generating or designing the camelized NANOBODY® is preferably a VH sequence from a mammal, more preferably, the VH sequence of a human being, such as a VH3 sequence. However, it should be noted that such camelized NANOBODIES® of the invention can be obtained in any suitable manner known per se (i.e., as indicated under points (1)-(8) above) and, thus, are not strictly limited to polypeptides that have been obtained using a polypeptide that comprises a naturally occurring VH domain as a starting material. For example, both "humanization" and "camelization" can be performed by providing a nucleotide sequence that encodes a naturally occurring $V_HH$ domain or VH domain, respectively, and then changing, in a manner known per se, one or more codons in the nucleotide sequence in such a way that the new nucleotide sequence encodes a "humanized" or "camelized" NANOBODY® of the invention, respectively. This nucleic acid can then be expressed in a manner known per se, so as to provide the desired NANOBODY® of the invention.

Alternatively, based on the amino acid sequence of a naturally occurring $V_HH$ domain or VH domain, respectively, the amino acid sequence of the desired humanized or camelized NANOBODY® of the invention, respectively, can be designed and then synthesized de novo using techniques for peptide synthesis known per se. Also, based on the amino acid sequence or nucleotide sequence of a naturally occurring $V_HH$ domain or VH domain, respectively, a nucleotide sequence encoding the desired humanized or camelized NANOBODY® hereof, respectively, can be designed and then synthesized de novo using techniques for nucleic acid synthesis known per se, after which the nucleic acid thus obtained can be expressed in a manner known per se, so as to provide the desired NANOBODY® of the invention. Other suitable methods and techniques for obtaining the NANOBODIES® hereof and/or nucleic acids encoding the same, starting from naturally occurring VH sequences or preferably $V_HH$ sequences, will be clear from the skilled person, and may, for example, comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide a NANOBODY® hereof or a nucleotide sequence or nucleic acid encoding the same.

According to one non-limiting aspect hereof, a NANOBODY® may be as defined herein, but with the proviso that it has at least "one amino acid difference" (as defined herein) in at least one of the framework regions compared to the corresponding framework region of a naturally occurring human VH domain, and, in particular, compared to the corresponding framework region of DP-47. More specifically, according to one non-limiting aspect of the invention, a NANOBODY® may be as defined herein, but with the proviso that it has at least "one amino acid difference" (as defined herein) at at least one of the Hallmark residues (including those at positions 108, 103 and/or 45) compared to the corresponding framework region of a naturally occurring human VH domain, and, in particular, compared to the corresponding framework region of DP-47. Usually, a NANOBODY® will have at least one such amino acid difference with a naturally occurring VH domain in at least one of FR2 and/or FR4, and, in particular, at at least one of the Hallmark residues in FR2 and/or FR4 (again, including those at positions 108, 103 and/or 45). Also, a humanized NANOBODY® hereof may be as defined herein, but with the proviso that it has at least "one amino acid difference" (as defined herein) in at least one of the framework regions compared to the corresponding framework region of a naturally occurring $V_HH$ domain. More specifically, according to one non-limiting aspect hereof, a NANOBODY® may be as defined herein, but with the proviso that it has at least "one amino acid difference" (as defined herein) at at least one of the Hallmark residues (including those at positions 108, 103 and/or 45) compared to the corresponding framework region of a naturally occurring $V_HH$ domain. Usually, a NANOBODY® will have at least one such amino acid difference with a naturally occurring $V_HH$ domain in at least one of FR2 and/or FR4, and, in particular, at at least one of the Hallmark residues in FR2 and/or FR4 (again, including those at positions 108, 103 and/or 45). As will be clear from the disclosure herein, it is also within the scope hereof to use natural or synthetic analogs, mutants, variants, alleles, homologs and orthologs (herein collectively referred to as "analogs") of the NANOBODIES® hereof as defined herein, and, in particular, analogs of the NANOBODIES® of SEQ ID NOS:6, 22 or 26. Thus, according to one embodiment, the term "NANOBODY® hereof" in its broadest sense also covers such analogs. Generally, in such analogs, one or more amino acid residues may have been replaced, deleted and/or added, compared to the NANOBODIES® hereof as defined herein. Such substitutions, insertions or deletions may be made in one or more of the framework regions and/or in one or more of the CDRs, and, in particular, analogs of the CDRs of the NANOBODIES® of SEQ ID NOS:6, 22 or 26, the CDRs corresponding with SEQ ID NOS:29-37 (see Table 1, FIGS. 1 and 5).

TABLE 1

CDRs of BACE1-specific NANOBODIES ®

| Nb | CDR1 | CDR2 | CDR3 |
|---|---|---|---|
| Nb_B9 (SEQ ID NO: 6) | EYTYGYCSMG (SEQ ID NO: 29) | TITSDGSTSYVDSVKG (SEQ ID NO: 30) | KTCANKLGAKFIS (SEQ ID NO: 31) |
| Nb_10C4 (SEQ ID NO: 22) | GYTYSTCSMA (SEQ ID NO: 32) | SIRNDGSTAYADSVKG (SEQ ID NO: 33) | RIGVGPGGTCSIYAPY (SEQ ID NO: 34) |
| Nb_4A2 (SEQ ID NO: 26) | GFTFETQYMT (SEQ ID NO: 35) | SINSGGTIKYYANSSV KG (SEQ ID NO: 36) | GQWAGVGAASS (SEQ ID NO: 37) |

When such substitutions, insertions or deletions are made in one or more of the framework regions, they may be made at one or more of the Hallmark residues and/or at one or more of the other positions in the framework residues. Substitutions, insertions or deletions at the Hallmark residues are generally less preferred (unless these are suitable humanizing substitutions as described herein). By means of non-limiting examples, a substitution may, for example, be a conservative substitution (as described herein) and/or an amino acid residue may be replaced by another amino acid residue that naturally occurs at the same position in another $V_HH$ domain. Thus, any one or more substitutions, deletions or insertions, or any combination thereof, that either improve the properties of the NANOBODY® hereof or that at least do not detract too much from the desired properties or from the balance or combination of desired properties of the NANOBODY® of the invention (i.e., to the extent that the NANOBODY® is no longer suited for its intended use) are included within the scope of the disclosure.

A skilled person will generally be able to determine and select suitable substitutions, deletions or insertions, or suitable combinations thereof, based on the disclosure herein and optionally after a limited degree of routine experimentation, which may, for example, involve introducing a limited number of possible substitutions and determining their influence on the properties of the NANOBODIES® thus obtained. For example, and depending on the host organism used to express the NANOBODY® or polypeptide of the disclosure, such deletions and/or substitutions may be designed in such a way that one or more sites for post-translational modification (such as one or more glycosylation sites) are removed, as will be within the ability of the person skilled in the art.

Alternatively, substitutions or insertions may be designed so as to introduce one or more sites for attachment of functional groups (as described herein), for example, to allow site-specific pegylation. One preferred class of analogs of the NANOBODIES® hereof comprise NANOBODIES® that have been humanized (i.e., compared to the sequence of a naturally occurring NANOBODY® of the invention). As mentioned in the background art cited herein, such humanization generally involves replacing one or more amino acid residues in the sequence of a naturally occurring $V_HH$ with the amino acid residues that occur at the same position in a human VH domain, such as a human VH3 domain.

Examples of possible humanizing substitutions or combinations of humanizing substitutions will be clear to the skilled person, from the possible humanizing substitutions mentioned in the background art cited herein, and/or from a comparison between the sequence of a NANOBODY® and the sequence of a naturally occurring human VH domain. The humanizing substitutions should be chosen such that the resulting humanized NANOBODIES® still retain the favorable properties of NANOBODIES® as defined herein and, more preferably, such that they are as described for analogs in the preceding paragraphs. A skilled person will generally be able to determine and select suitable humanizing substitutions or suitable combinations of humanizing substitutions, based on the disclosure herein and optionally after a limited degree of routine experimentation, which may, for example, involve introducing a limited number of possible humanizing substitutions and determining their influence on the properties of the NANOBODIES® thus obtained. Generally, as a result of humanization, the NANOBODIES® of the disclosure may become more "human-like," while still retaining the favorable properties of the NANOBODIES® of the invention as described herein. As a result, such humanized NANOBODIES® may have several advantages, such as a reduced immunogenicity, compared to the corresponding naturally occurring $V_HH$ domains.

Again, based on the disclosure herein and optionally after a limited degree of routine experimentation, the skilled person will be able to select humanizing substitutions or suitable combinations of humanizing substitutions that optimize or achieve a desired or suitable balance between the favorable properties provided by the humanizing substitutions on the one hand and the favorable properties of naturally occurring $V_HH$ domains on the other hand. Examples of such modifications, as well as examples of amino acid residues within the NANOBODY® sequence that can be modified in such a manner (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the NANOBODY® of the invention, and, in particular, of one or more functional groups, residues or moieties that confer one or more desired properties or functionalities to the NANOBODY® of the invention.

Examples of such functional groups and of techniques for introducing them will be clear to the skilled person, and can generally comprise all functional groups and techniques mentioned in the general background art cited hereinabove, as well as the functional groups and techniques known per se for the modification of pharmaceutical proteins and, in particular, for the modification of antibodies or antibody fragments (including ScFvs and single domain antibodies), for which reference is, for example, made to *Remington's Pharmaceutical Sciences*, 16th ed., Mack Publishing Co., Easton, Pa. (1980). Such functional groups may, for example, be linked directly (for example, covalently) to a NANOBODY® of the invention, or optionally, via a suitable linker or spacer, as will again be clear to the skilled person.

One of the most widely used techniques for increasing the half-life and/or reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including, but not limited to, (single) domain antibodies and ScFvs); reference is made to, for example, Chapman, *Nat. Biotechnol.* 54:531-545 (2002); by Veronese and Harris, *Adv. Drug Deliv. Rev.* 54:453-456 (2003); by Harris and Chess, *Nat. Rev. Drug Discov.* 2 (2003); and in WO04060965. Various reagents for pegylation of proteins are also commercially available, for example, from Nektar Therapeutics, USA. Preferably, site-directed pegylation is used, in particular, via a cysteine-residue (see, for example, Yang et al., *Protein Engineering* 16, 10:761-770 (2003). For example, for this purpose, PEG may be attached to a cysteine residue that naturally occurs in a NANOBODY® hereof. A NANOBODY® hereof may be modified so as to suitably introduce one or more cysteine residues for attachment of PEG, or an amino acid sequence comprising one or more cysteine residues for attachment of PEG may be fused to the N- and/or C-terminus of a NANOBODY® hereof, all using techniques of protein engineering known per se to the skilled person. Preferably, for the NANOBODIES® and proteins of the disclosure, a PEG is used with a molecular weight of more than 5000, such as more than 10,000 and less than 200,000, such as less than 100,000; for example, in the range of 20,000-80,000.

Another, usually less preferred modification comprises N-linked or O-linked glycosylation, usually as part of co-translational and/or post-translational modification, depending on the host cell used for expressing the NANOBODY® or polypeptide of the disclosure. Yet another modification may comprise the introduction of one or more detectable labels or other signal-generating groups or moieties, depending on the intended use of the labeled NANOBODY®. Suitable labels and techniques for attaching, using and detecting them will be clear to the skilled person and, for example, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metal chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person and, for example, include moieties that can be detected using NMR or ESR spectroscopy. Such labeled NANOBODIES® and polypeptides of the disclosure may, for example, be used for in vitro, in vivo or in situ assays (including immunoassays known per se, such as ELISA, RIA, EIA and other "sandwich assays," etc.) as well as in vivo diagnostic and imaging purposes, depending on the choice of the specific label.

As will be clear to the skilled person, another modification may involve the introduction of a chelating group, for example, to chelate one of the metals or metallic cations referred to above. Suitable chelating groups include, for example, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the NANOBODY® of the invention to another protein, polypeptide or chemical compound that is bound to the other half of the binding pair, i.e., through formation of the binding pair. For example, a NANOBODY® hereof may be conjugated to biotin, and linked to another protein, polypeptide, compound or carrier conjugated to avidin or streptavidin. For example, such a conjugated NANOBODY® may be used as a reporter, for example, in a diagnostic system where a detectable signal-producing agent is conjugated to avidin or streptavidin. Such binding pairs may, for example, also be used to bind the NANOBODY® of the invention to a carrier, including carriers suitable for pharmaceutical purposes. One non-limiting example is the liposomal formulations described by Cao and Suresh, *Journal of Drug Targeting* 8, 4:257 (2000). Such binding pairs may also be used to link a therapeutically active agent to the NANOBODY® hereof.

It is expected that the NANOBODIES® and polypeptides of the disclosure will generally bind to all naturally occurring or synthetic analogs, variants, mutants, alleles, parts and fragments of BACE1, or at least to those analogs, variants, mutants, alleles, parts and fragments of BACE1, that contain one or more antigenic determinants or epitopes that are essentially the same as the antigenic determinant(s) or epitope(s) to which the NANOBODIES® and polypeptides of the disclosure bind in BACE1 (e.g., in wild-type BACE1). Again, in such a case, the NANOBODIES® and polypeptides of the disclosure may bind to such analogs, variants, mutants, alleles, parts and fragments with an affinity and/or specificity that are the same as, or different from (i.e., higher than or lower than), the affinity and specificity with which the NANOBODIES® hereof bind to (wild-type) BACE1.

It is also included within the scope hereof that the NANOBODIES® and polypeptides of the disclosure bind to some analogs, variants, mutants, alleles, parts and fragments of BACE1, but not to others. Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example, from WO04037999, WO9849185, WO0046383 and WO0109300; and (preferred) types and/or combinations of such substitutions may be selected on the basis of the pertinent teachings from WO04037999, as well as WO9849185. Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, His, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; His into Leu or into Val; Leu into His or into Val; Lys into Arg, into Gln or into Glu; Met into Leu, into Tyr or into His; Phe into Met, into Leu or into Tyr; Ser into Thr; Thr into Ser; Trp into Tyr; Tyr into Trp; and/or Phe into Val, into His or into Leu.

Polypeptide therapeutics and, in particular, antibody-based therapeutics, have significant potential as drugs because they have exquisite specificity to their target and a low inherent toxicity. However, it is known by the skilled person that an antibody that has been obtained for a therapeutically useful target requires additional modification in order to prepare it for human therapy, so as to avoid an unwanted immunological reaction in a human individual upon administration. The modification process is commonly termed "humanization." It is known by the skilled artisan that antibodies raised in species, other than in humans, require humanization to render the antibody therapeutically useful in humans ((1) CDR grafting: Protein Design Labs: U.S. Pat. Nos. 6,180,370, 5,693,761; Genentech U.S. Pat.

No. 6,054,297; Celltech: EP626390, U.S. Pat. No. 5,859, 205; (2) Veneering: Xoma: U.S. Pat. Nos. 5,869,619, 5,766, 886, 5,821,123). There is a need for a method for producing antibodies that avoids the requirement for substantial humanization or that completely obviates the need for humanization.

There is a need for a new class of antibodies that have defined framework regions or amino acid residues and that can be administered to a human subject without the requirement for substantial humanization, or the need for humanization at all. According to one aspect of the invention, NANOBODIES® are polypeptides that are derived from heavy chain antibodies and whose framework regions and complementary determining regions are part of a single domain polypeptide. Examples of such heavy chain antibodies include, but are not limited to, naturally occurring immunoglobulins devoid of light chains. Such immunoglobulins are disclosed in WO9404678, for example. The antigen-binding site of this unusual class of heavy chain antibodies has a unique structure that comprises a single variable domain. For clarity reasons, the variable domain derived from a heavy chain antibody naturally devoid of light chain is known herein as a $V_H H$ or $V_H H$ domain or NANOBODY®. Such a $V_H H$ domain peptide can be derived from antibodies raised in Camelidae species, for example, in camel, dromedary, llama, alpaca and guanaco. Other species besides Camelidae (e.g., shark, pufferfish) may produce functional antigen-binding heavy chain antibodies naturally devoid of light chain. $V_H H$ domains derived from such heavy chain antibodies are within the scope of the invention.

Camelidae antibodies express a unique, extensive repertoire of functional heavy chain antibodies that lack light chains. The $V_H H$ molecules derived from Camelidae antibodies are the smallest intact antigen-binding domains known (approximately 15 kDa, or ten times smaller than conventional IgG) and, hence, are well suited toward delivery to dense tissues and for accessing the limited space between macromolecules. Other examples of NANOBODIES® include NANOBODIES® derived from VH domains of conventional four-chain antibodies that have been modified by substituting one or more amino acid residues with Camelidae-specific residues (the so-called camelization of heavy chain antibodies, WO9404678). Such positions may preferentially occur at the VH-VL interface and at the so-called Camelidae hallmark residues (WO9404678), comprising positions 37, 44, 45, 47, 103 and 108. NANOBODIES® correspond to small, robust and efficient recognition units formed by a single immunoglobulin (Ig) domain.

A "fragment of a NANOBODY®" as used herein refers to less than 100% of the sequence (e.g., 99%, 90%, 80%, 70%, 60%, 50%, 40%, 30%, 20%, 10% etc.), but comprising 5, 6, 7, 8, 9, 10, 12, 13, 14, 15, 16, 17, 18, 19, 20, 21, 22, 23, 24, 25 or more amino acids. A fragment is preferably of sufficient length such that the interaction of interest is maintained with affinity of $1 \times 10^6$ M or better. A "fragment" as used herein also refers to optional insertions, deletions and substitutions of one or more amino acids that do not substantially alter the ability of the target to bind to a NANOBODY® raised against the wild-type target. The number of amino acid insertions, deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids. One embodiment of the present invention relates to a polypeptide comprising at least one NANOBODY® wherein one or more amino acid residues have been substituted without substantially altering the antigen binding capacity.

In a particular embodiment, the antibody of the invention is bivalent and formed by bonding together, chemically or by recombinant DNA techniques, two monovalent single domains of heavy chains. In another particular embodiment, the antibody of the invention is bi-specific and formed by bonding together two variable domains of heavy chains, each with a different specificity (i.e., one with a specificity for BACE1 and the other one with a specificity for a neuron, such as, for example, ICAM5 or telencephalin). Similarly, polypeptides comprising multivalent or multi-specific single domain antibodies are included here as non-limiting examples.

In yet another embodiment, a single domain antibody that is capable of preventing the uptake of BACE1 can be used as a medicament. In yet another embodiment, a single domain antibody that comprises at least one of the complementarity-determining regions (CDRs) with an amino acid sequence selected from the group comprising SEQ ID NOS:29-37 can be used as a medicament. In yet another embodiment, a single domain antibody, which amino acid comprises SEQ ID NOS:6, 22 or 26, can be used as a medicament.

In yet another embodiment, a single domain antibody that is capable of preventing the uptake of pro-BACE1 can be used for the manufacture of a medicament to treat diseases associated with an overexpression of BACE1. An example of a disease where an overexpression of BACE1 occurs is Alzheimer's disease. In general, "therapeutically effective amount," "therapeutically effective dose" and "effective amount" means the amount needed to achieve the desired result or results (inhibiting BACE1 binding; treating or preventing Alzheimer's disease). One of ordinary skill in the art will recognize that the potency and, therefore, an "effective amount" can vary for the NANOBODY® that inhibits BACE1 binding used in the invention. One skilled in the art can readily assess the potency of the NANOBODY®. By "pharmaceutically acceptable" is meant a material that is not biologically or otherwise undesirable, i.e., the material may be administered to an individual along with the compound without causing any undesirable biological effects or interacting in a deleterious manner with any of the other components of the pharmaceutical composition in which it is contained.

The term "medicament to treat" relates to a composition comprising antibodies as described above and a pharmaceutically acceptable carrier or excipient (both terms can be used interchangeably) to treat or to prevent diseases as described herein. The administration of a NANOBODY® as described above or a pharmaceutically acceptable salt thereof may be by way of oral, inhaled or parenteral administration. In particular embodiments, the NANOBODY® is delivered through intrathecal or intracerebroventricular administration. The active compound may be administered alone or preferably formulated as a pharmaceutical composition.

An amount effective to treat Alzheimer's disease that expresses the antigen recognized by the NANOBODY® depends on the usual factors, such as the nature and severity of the disorder being treated and the weight of the mammal. However, a unit dose will normally be in the range of 0.01 to 50 mg, for example, 0.01 to 10 mg, or 0.05 to 2 mg of NANOBODY® or a pharmaceutically acceptable salt thereof. Unit doses will normally be administered once or more than once a day, for example, two, three, or four times a day, more usually one to three times a day, such that the total daily dose is normally in the range of 0.0001 to 1 mg/kg; thus a suitable total daily dose for a 70 kg adult is 0.01 to 50 mg, for example, 0.01 to 10 mg or more, usually 0.05 to 10 mg.

In certain embodiments, the compound or a pharmaceutically acceptable salt thereof is administered in the form of a unit-dose composition, such as a unit dose oral, parenteral, or inhaled composition. Such compositions are prepared by admixture and are suitably adapted for oral, inhaled or parenteral administration and, as such, may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tableting agents, lubricants, disintegrants, colorants, flavorings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycolate. Suitable lubricants include, for example, magnesium stearate. Suitable pharmaceutically acceptable wetting agents include sodium lauryl sulphate. These solid oral compositions may be prepared by conventional methods of blending, filling, tableting, or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example, sorbitol, syrup, methyl cellulose, gelatin, hydroxyethylcellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example, methyl or propyl p-hydroxybenzoate or sorbic acid, and, if desired, conventional flavoring or coloring agents. Oral formulations also include conventional sustained release formulations, such as tablets or granules having an enteric coating.

Preferably, compositions for inhalation are presented for administration to the respiratory tract as a snuff or an aerosol or solution for a nebulizer, or as a microtine powder for insufflation, alone or in combination with an inert carrier such as lactose. In such a case, the particles of active compound suitably have diameters of less than 50 microns, preferably less than 10 microns, for example, between 1 and 5 microns, such as between 2 and 5 microns. A favored inhaled dose will be in the range of 0.05 to 2 mg, for example, 0.05 to 0.5 mg, 0.1 to 1 mg or 0.5 to 2 mg.

For parenteral administration, fluid unit dose forms are prepared containing a compound of the present invention and a sterile vehicle. The active compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilized by exposure to ethylene oxide before suspending in the sterile vehicle.

Advantageously, a surfactant or wetting agent is included in the composition to facilitate uniform distribution of the active compound. Where appropriate, small amounts of bronchodilators, for example, sympathomimetic amines such as isoprenaline, isoetharine, salbutamol, phenylephrine and ephedrine; xanthine derivatives such as theophylline and aminophylline; corticosteroids such as prednisolone; and adrenal stimulants such as ACTH, may be included. As is common practice, the compositions will usually be accompanied by written or printed directions for use in the medical treatment concerned.

In yet another embodiment, one or more single domain antibodies of the invention can be linked (optionally, via one or more suitable linker sequences) to one or more (such as two and preferably one) amino acid sequences that allow the resulting polypeptide of the invention to cross the blood brain barrier. In particular, the one or more amino acid sequences that allow the resulting polypeptides of the invention to cross the blood brain barrier may be one or more (such as two and preferably one) NANOBODIES®, such as the NANOBODIES® described in WO 02/057445, of which FC44 (SEQ ID NO:189 of WO 06/040153) and FC5 (SEQ ID NO:190 of WO 06/040154) are preferred examples.

The present invention further provides a pharmaceutical composition for use in the treatment and/or prophylaxis of herein-described disorders, which comprises a pharmaceutically acceptable salt thereof, or a pharmaceutically acceptable solvate thereof, and, if required, a pharmaceutically acceptable carrier thereof.

It should be clear that the therapeutic method hereof for addressing Alzheimer's disease can also be used in combination with any other AD disease therapy known in the art, such as gamma-secretase inhibitors or other beta-secretase inhibitors.

In a particular embodiment, the single domain antibodies hereof can be used for the preparation of a diagnostic assay. BACE1 can be detected in a variety of cells and tissues, especially in brain cells and tissues, wherein the degree of expression corroborates with the severity of Alzheimer's disease. Therefore, there is provided a method of in situ detecting localization and distribution of BACE1 expression in a biological sample. The method comprises the step of reacting the biological sample with a detectable BACE1 NANOBODY® and detecting the localization and distribution of the detectable NANOBODY®. The term "biological sample" refers to cells and tissues, including, but not limited to, brain cells and tissues. The term further relates to body fluids.

Therefore, there is provided a method of detecting BACE1 protein in a body fluid of a patient. The method comprises the steps of reacting the body fluid with an anti-BACE1 NANOBODY® hereof and monitoring the reaction. The body fluid is, for example, plasma, urine, cerebrospinal fluid, pleural effusions or saliva. Monitoring the reaction may be effected by having the NANOBODY® labeled with a detectable moiety, or to use its constant region as an inherent detectable moiety, to which a second antibody, which includes a detectable moiety, can specifically bind. CSF BACE1 can, for example, be detected in patients suffering from Alzheimer's disease. According to a preferred embodiment of the present invention, reacting the body fluid with the anti-BACE1 NANOBODY® is effected in solution.

Alternatively, reacting the body fluid with the anti-BACE1 NANOBODY® is effected on a substrate capable of adsorbing proteins present in the body fluid, all as well known in the art of antibody-based diagnosis. Further, according to the disclosure, there is provided a method of detecting the presence, absence or level of BACE1 protein in a biological sample. The method comprises the following steps. First, proteins are extracted from the biological sample, thereby a plurality of proteins are obtained. The protein extract may be a crude extract and can also include non-proteinaceous material. Second, the proteins are size separated, e.g., by electrophoresis, gel filtration, etc. Fourth, the size-separated proteins are interacted with an anti-BACE1 NANOBODY®. Finally, the presence, absence or level of the interacted anti-BACE1 NANOBODY® is detected. In case of gel electrophoresis, the interaction with the NANOBODY® is typically performed following blotting of the size-separated proteins onto a solid support (membrane).

The following examples more fully illustrate the disclosure. Starting materials and reagents disclosed below are known to those skilled in the art, and are available commercially or can be prepared using well-known techniques.

EXAMPLES

1. Generation and Isolation of BACE1-Specific NANOBODIES®

To generate BACE1-specific antibodies, a dromedary was immunized six times with recombinant human BACE1 over a period of about six weeks. After this period, a BACE1-specific humoral response, as assessed by ELISA, was observed for each of the three different IgG subclasses that exist in Camelidae, namely the conventional IgG1 molecules and the heavy chain-only subclasses IgG2 and IgG3 (IgG classes reviewed in Conrath et al., 2003). The variable chain of the HCAbs ($V_HH$), which contains the antigen-binding fragment, was amplified from isolated dromedary lymphocytes and cloned into a pHEN4 phagemid vector to generate a library of $4 \times 10^7$ individual transformants. After rescuing this bank with M13K07 helper phages, the $V_HH$ repertoire was expressed on the surface of bacteriophages. With these phages, BACE1-specific $V_HHs$ could be isolated from the whole $V_HH$ pool using panning, an in vitro selection technique (reviewed in Smith and Petrenko, 1997). For this, the phages were incubated onto a solid phase passively coated with the immunogen. After washing, bound phages were eluted and used to infect exponentially growing E. coli TG1 cells to produce new virions. These virions were used in a next selection round in order to enrich for BACE1-specific binders. After two to three consecutive rounds of panning, individual colonies were randomly picked and incubated with IPTG to induce expression of the NANOBODIES®. The $V_HH$ protein fragments were extracted from the bacterial periplasm and tested individually by ELISA for their ability to interact with BACE1. The positive scoring clones were sequenced and, as such, twenty different specific NANOBODIES® were identified.

2. Sequence Analysis of the BACE1-Binders

Fourteen out of the twenty selected BACE1-binders are clearly derived from $V_HH$ germ-line genes: Nb_B1, Nb_B2, Nb_B3, Nb_B5, Nb_B8, Nb_B9, Nb_B10, Nb_B11, Nb_B12, Nb_B15, Nb_B16, Nb_B21, Nb_B25, and Nb_B26, corresponding with SEQ ID NOS:1-14, respectively (FIG. 1). The amino acid sequence of their framework-2 (FR2) region resembles that of a typical $V_HH$ FR2 (Muyldermans et al., 1994), with residues F/Y, E/Q, R/C and G at positions 37, 44, 45 and 47, respectively (numbering according to Kabat et al., 1991). However, the remaining six antibody fragments, Nb_B4, Nb_B6, Nb_B7, Nb_B13, Nb_B14 and Nb_B24 (corresponding with SEQ ID NOS: 38-43, respectively), seem to originate from conventional antibody germ-line genes, since they contain the $V_{37}G_{44}L_{45}W_{47}$ tetrad, a typical hallmark that distinguishes the variable domain of the heavy chain of conventional antibodies ($V_H$) from $V_HH$ fragments at the germline level. These hallmark residues are critically required in $H_2$-$L_2$ antibodies for the association of the heavy chain with a light chain.

Due to the high sequence similarity of the six $V_H$-like NANOBODIES®, it is most likely they are all derived from one and the same B cell lineage. The differences in amino acid sequence could be the result of the ongoing somatic hypermutation of the antibody gene fragments in maturing B cells and the subsequent antigen-driven selection, a continuous process leading to ever better fitting antibodies. The six $V_H$-like NANOBODIES® also differ from the other binders in that they contain a leucine residue at position 11 in their framework-1 (FR1), another characteristic of $V_H$ genes that is important for the interaction with a light chain (Lesk and Chothia, 1988; Padlan, 1994).

In a typical $V_HH$ FR1, this Leu residue is often replaced by a smaller and hydrophilic residue, usually a serine, as seen in the 14 BACE1 binders with a true $V_HH$ motif. The $V_H$-like molecules all have a short CDR3 of only six amino acids, whereas, the other binders have significantly larger H3 loops, ranging from 13 to 21 residues, with an average length of 17. This is consistent with the average $V_HH$-CDR3 length of 15 to 16 residues reported before in literature (reviewed in Muyldermans and Lauwereys, 1999).

In general, the CDR2 and CDR1 of $V_HHs$ consist of 16 to 17 and 10 residues, respectively, but about 30% of dromedary $V_HH$ cDNAs were reported to be off-sized. This does not adversely affect their function, but instead, even increases the antigen-binding repertoire (Nguyen et al., 2000). Unusual CDR1 and CDR2 lengths are also observed for our BACE1 binders. The CDR2 of Nb_B15 contains 19 residues due to a tandem repetition of two amino acids, whereas, that of Nb_B21 consists of 18 residues. Aberrant CDR1 sizes are found in Nb_B1, Nb_B15 and Nb_B16 due to an insertion, a deletion of one amino acid and a deletion of two residues, respectively. Finally, Nb_B25 has an unusually long framework-3 region with a tandem repetition of two amino acid residues. Deviating lengths in the BACE1-binders are due to changes located at three typical $V_HH$ insertion/deletion hot spots, surrounding residues 30±3, 54±3 and 74±1. These hot spots can be found within or at the border of peculiar DNA sequences, such as palindromic sequences (corresponding to residues 30-33 and 54-57) or heptamer-like sequences of an Ig recombination signal (often found at residues 76-78) (Nguyen et al., 2000).

Besides the conserved disulphide bridge between $Cys_{22}$ and $Cys_{92}$, extra non-canonical cysteine residues do not frequently occur in conventional antibodies, although they are not totally excluded. However, an additional pair of cysteines is encountered in 75% of reported dromedary $V_HHs$ (Arbabi Ghahroudi et al., 1997; Lauwereys et al., 1998; Conrath et al., 2001a; Saerens et al., 2004). One of these extra cysteine residues is typically located within the CDR3 loop, whereas, the other one can be found either on position 30, 32 or 33 within the CDR1 or at position 45 in FR2. Since the $V_HH$ CDR3 loop folds back onto the CDR1-FR2 region, the two cysteine residues come into contact distance and are likely engaged into an interloop disulphide bond that cross-links the antigen-binding loops (Desmyter et al., 1996). Such a bond reduces flexibility of the long CDR3 loop and thus provides increased stability. Besides, the interloop bond might lead to a constrained, but new conformation of the CDR loops, thereby increasing the antigen-binding repertoire.

Compared to the percentages known from literature, there is a low incidence of additional cysteines in the BACE1 binders. A putative additional disulphide bond is only present in four out of the 14 NANOBODIES® with $V_HH$ motif Nb_B25 has a cysteine residue at position 33 within the CDR1; Nb_B9 has one at position 32; and in Nb_B5, an additional bridge will probably be formed between $Cys_{45}$ and the CDR3. A cysteine at position 53, as seen in Nb_B12, has been described so far for neither dromedary, nor llama $V_HHs$.

3. Defining Affinities of the BACE1-Binders for their Immunogen at pH 7.0 and pH 5.0

The cDNAs of the 20 isolated BACE1-binders were subcloned into the pHEN6 prokaryotic expression vector and expressed in *E. coli* WK6 cells to produce his-tagged soluble proteins. The recombinant $V_HHs$ were subsequently purified by Ni-NTA affinity chromatography, followed by size-exclusion chromatography. The expression levels of the distinct clones varied between 1 and 15 mg per liter of culture medium. The affinity of all $V_HHs$ for BACE1 was determined quantitatively using the surface plasmon resonance technology on Biacore 3000. Each of the different $V_HHs$ was injected at concentrations ranging from 0 to 0.5 µM on a chip onto which BACE1 was coupled. Binding was evaluated both at pH 7.0 and pH 5.0. Measurements at pH 5.0 were included because a firm interaction between BACE1 and a $V_HH$ should be preserved at this pH, since the endosomal compartment with its slightly acidic content was reported to be the major subcellular site of β-site cleavage of APP (Koo, 1994). Besides, BACE1 was shown to have optimal β-secretase activity at about pH 5.0 in vitro (Sinha et al., 1999; Vassar et al., 1999; Yan et al., 1999; Lin et al., 2000). The dissociation constants obtained for all $V_HHs$ vary between 4 and 669 nM at pH 7.0 and between 4.2 nM and 6.8 µM at pH 5.0 (FIG. 2, Panel A). The majority of the binders have dissociation constants between 10 and 100 nM at both pH conditions.

4. Capacity of the Different $V_HHs$ to Pull Down Native BACE1

For the immunization of the dromedary, the isolation of the BACE1-specific binders during panning and the in vitro affinity measurements by Biacore, we used recombinant human soluble BACE1, completely devoid of carbohydrate chains. This recombinant protein, supplied by Dr. S. Masure (Johnson & Johnson, Beerse, Belgium) was obtained from an insect cell expression system using slightly truncated BACE1 cDNA in which the four N-glycosylation sites and the whole membrane anchor were removed (Bruinzeel et al., 2002). It is not unthinkable that epitopes that are easily accessible in the "naked" BACE1, used for the immunization, are shielded by glycan chains or other post-translational modifications of BACE1 proteins generated in mammalian cells. Therefore, we wondered whether the selected binders would all be able to recognize glycosylated BACE1 expressed in mammalian cells.

To test this, 2 µg of his-tagged $V_HH$ molecules were incubated with 4 µg of total protein extract from COS cells transiently transfected with human BACE1 cDNA. Nickel-beads were subsequently used to pull down the $V_HH$ molecules together with the bound proteins. After extensive washing, bound proteins were eluted, separated by SDS-PAGE and BACE1 protein was detected by Western blotting using a rabbit polyclonal BACE1-specific antibody (ProSci, 2253) (FIG. 2, Panel B). $V_HH$ proteins raised against either Aβ (Nb_Aβ3) or beta-lactamase BCII 569/H (Nb_BCIILP) (Conrath et al., 2001a), were used as negative controls and were unable to capture BACE1 from the cell lysate, as expected. Five binders, Nb_B7, Nb_B9, Nb_B10, Nb_B13 and Nb_B24 have the highest efficacy to pull down BACE1 compared to the other NANOBODIES®. For Nb_B3, Nb_B8, Nb_B12 and Nb_B21 at the best a trifling trace of coprecipitated BACE1 can be detected after overnight exposure.

Note that in the group of the 6 $V_H$-like NANOBODIES® (Nb_B4, Nb_B6, Nb_B7, Nb_B13, Nb_B14 and Nb_B24), huge differences are observed in the ability of each NANOBODY® to bind to glycosylated BACE1, even though they probably originated from the same B-cell lineage. Despite a high overall sequence similarity of about 90%, Nb_B13 and Nb_B14 share only 70% of amino acids in their antigen-binding CDR regions and this difference apparently is sufficient to adversely affect the affinity of Nb_B14 for its antigen when compared to Nb_B13.

5. Effect of Ectopic Expression of the NANOBODIES® on BACE Inhibition

In a next step, we decided to express some of the $V_HHs$ into mammalian cells. Thereto, COS1-B1 cells, stably expressing low levels of BACE1, were co-transfected with APPSw and either Nb_B26 or Nb_B9. Control cells were either transfected with empty vector or with APPSw alone. The cDNAs (of Nb_B26 or Nb_B9) were cloned into a eukaryotic expression vector, downstream of the signal peptide of BACE1 and with a myc-epitope tag at its C-terminus (FIG. 3, Panel A). The signal sequence ensures translocation of the newly formed protein into the secretory pathway, where the $V_HH$ should encounter its antigen, the ectodomain of BACE1. $APP_{Sw}$ and the two $V_HHs$ were co-transfected into COS cells stably expressing low levels of human BACE1 (COS-B1 cells). These cells have detectable, but not saturated, levels of β-secretase activity and are easily transfected using liposome-based transfection reagents. Two days after transfection, cell extracts were prepared, proteins were separated by SDS-PAGE and transferred to a nitrocellulose membrane. Using rabbit polyclonal B63.1 as a primary antibody and GARIR, an infrared-coupled secondary antibody, the APP C-terminal fragments were visualized and quantified by the ODYSSEY® Infrared Imaging System (FIG. 3, Panels B and C). Again, Nb_B26 had no effect on APP processing. The ratio of β-CTF on total APP CTFs is equal to that of non-treated cells (FIG. 3, Panel C). Nb_B9 consistently decreased β-secretase activity by about 30% (p<0.001), even though it was expressed at much lower levels than Nb_B26 (FIG. 3, Panel B). This decrease occurred in the absence of any effect on BACE1 protein levels, ruling out the possibility that the NANOBODY® affects BACE1 protein stability.

6. Effect of Addition of Extracellular NANOBODIES® on APP Processing in Cells

In a next step, NANOBODY® Nb_B9 was tested as to whether it could also affect APP processing when added to culture medium of cells. At least part of BACE1 is directed to the plasma membrane before being targeted to endosomes, so BACE1-specific antibodies could potentially bind to the ectodomain at the cell surface and be smuggled inside cells by co-internalization with their antigen. Since β-secretase cleavage of wild-type APP predominantly occurs within the endosomal compartments, neutralizing the enzyme's activity from the plasma membrane might be sufficient to decrease β-site APP proteolysis. SH-SY5Y cells, neuroblastoma cells with relatively high endogenous BACE1 activity, were infected with recombinant adenoviruses containing the cDNA encoding either human APP wild-type or the FAD APP$_{Sw}$ mutant. The FAD mutant was included since it is a much better BACE1 substrate, which enables easier detection of Aβ and β-CTF. However, the majority of APP$_{Sw}$ has been shown to be cleaved at the β-site in the secretory pathway before reaching the plasma membrane (Martin et al., 1995; Thinakaran et al., 1996), so BACE1-neutralizing V$_H$Hs binding at the cell surface might not be capable of preventing β-site APP$_{Sw}$ cleavage.

Two days after adenoviral infection, the SH-SY5Y cells were radioactively labeled and incubated with 2 μM Nb_B9 for six hours. The conditioned medium was used to immunoprecipitate secreted Aβ, whereas, APP full-length and C-terminal fragments were pulled down from cell lysates. APP fragments were separated by SDS-PAGE. Gels were fixed, dried and analyzed by phosphorimaging. The presence of Nb_B9 caused clear detectable change in amounts of β-CTF or Aβ compared to non-treated cells (FIG. 4).

7. Isolation of other BACE1-Specific NANOBODIES®

Further, a new screening of the V$_H$H phage libraries was performed using a different panning strategy, while Nb_B9 was included for further analysis. Phage pannings of the two V$_H$H libraries were performed using biotinylated antigen (the ectodomain of human BACE1). After three rounds of consecutive panning, 500 single colonies were randomly picked for phage ELISA screening. One hundred fifty-eight out of 500 colonies scored positive in phage ELISA screening. The positive colonies were further screened by periplasmic extract ELISA; 44 colonies out the 158 colonies were scored positive. The positive colonies isolated from periplasmic extract ELISA screening were analyzed by PCR and restriction enzyme digestion to group them according to restriction pattern and for further sequencing analysis. Fourteen new V$_H$Hs were identified from the screening.

The alignment of the V$_H$Hs sequence was listed in FIG. 5. Among these V$_H$Hs, ten clones (1B3, 10C2, 12B6 10B5, 13A5, 2C6, 6A4, 10C4, 13B6 and 1A4 (SEQ ID NOS:15-24, respectively)) were isolated from the dromedary libraries, and four clones (2B6, 4A2, 1D4 and 9D3 (SEQ ID NOS:25-28, respectively)) were isolated from the llama library. The cDNA of these clones were subcloned into expression vector pHEN6 and V$_H$H antibodies were then purified for functional assay tests.

Figure 6:
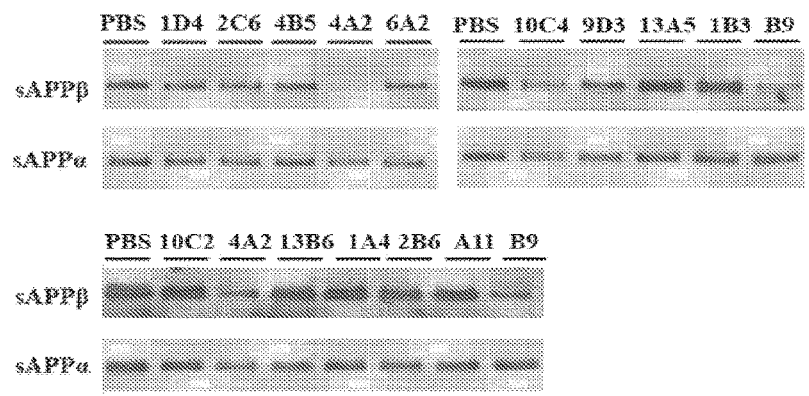
FIG. 6: Western blot analysis of sAPPβ and sAPPα from conditioned medium of neuroblastoma cells SH-SY5Y/APPwt treated with NANOBODIES® by adding to the medium at final concentration of 20 µM. Cells treated with NANOBODY® B9 (SEQ ID NO:6), 10C4 (SEQ ID NO:22), and 4A2 (SEQ ID NO:26) showed a significant decrease in sAPPβ producing.
Figure 7:
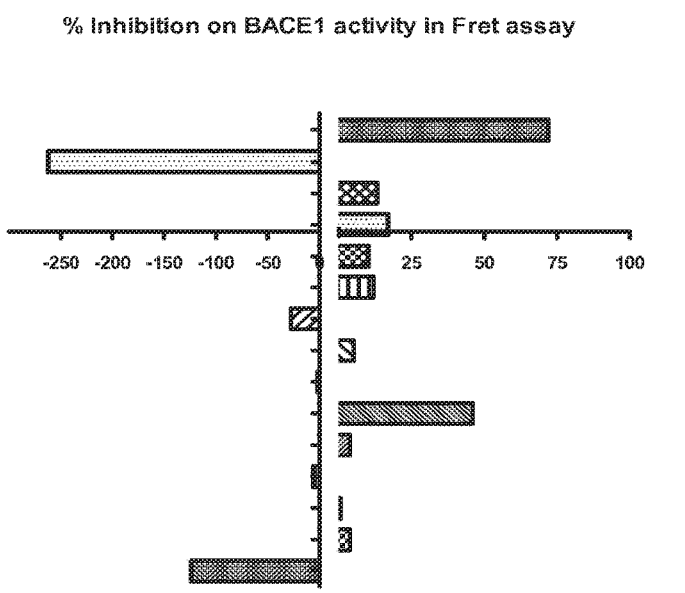
FIG. 7: The inhibition effects of different NANOBODIES® (10 µM) on BACE1 activity in FRET assay at a concentration of 10 µM. In this cell-free enzymatic assay, Nb_B9 (SEQ ID NO:6), Nb_10C4 (SEQ ID NO:22), Nb_4A2 (SEQ ID NO:26), and Nb_1B3 (SEQ ID NO:15) significantly modulate BACE1 activity.

8. BACE1-Specific NANOBODIES® Inhibit BACE1 Activity in a Cellular Assay and Modulate BACE1 Activity in a Cell-Free Enzymatic Assay All 15 V$_H$Hs (14 new V$_H$Hs+Nb_B9) were first tested in a cellular assay by adding them to the medium of SH-SY5Y cells stably expressing APPwt at a final concentration of 20 μM. As shown in FIG. 6, cells treated with V$_H$Hs B9, 10C4, 4A2 for 24 hours were shown to decrease sAPPβ generation while sAPPα levels in the conditioned medium remained the same as that of control, suggesting BACE1 activity was inhibited by these V$_H$Hs in the cellular assay.

In parallel, the capacity of the V$_H$Hs to modulate β-secretase activity was tested in an in vitro β-secretase assay that is based on the Fluorescence Resonance Energy Transfer (FRET) technology. This assay makes use of a synthetic peptide substrate that mimics the BACE1 cleavage site of APP and is coupled to a fluorophore on its N-terminus and a fluorescence acceptor on its C-terminus. The light emitted by the fluorophore is absorbed by the fluorescence acceptor as long as these two moieties are in close proximity. Only upon proteolysis, when recombinant BACE1 is added to the synthetic substrate, energy transfer no longer occurs and the amount of light emitted, which is linearly related to the amount of cleaved product and, hence, to the β-secretase activity, can be measured. All V$_H$Hs were tested by this BACE1 FRET assay at a final concentration of 10 μM.

As shown in FIG. 7, 10C4 and 4A2, the two candidate BACE1 inhibitors identified in the cellular assays, inhibited BACE1 activity in the FRET assay. Interestingly, B9, the candidate inhibitor isolated from the cellular assay, was shown to increase 260% of BACE1 activity in the FRET assay. Another clone, 1B3 was also shown to increase 125% of BACE1 activity in the FRET assay, although it had no apparent effect on BACE1 in the cellular assay. The remaining V$_H$Hs had no or negligible effects on BACE1 activity in the FRET assay.

The dose-response curves of 10C4, 4A2 and B9 on BACE1 activity were established by FRET assay. As shown in FIG. 8, 10C4 could inhibit maximal ~70% of BACE1 activity and the IC50 was 150 nM. 4A2 could inhibit maximal ~40% of BACE1 activity and the IC50 was 1.2 μM. B9 could increase BACE1 activity up to 3.5 times with ~100 nM concentration, and the EC50 in the response curve was 4.1 nM.

Figure 9:
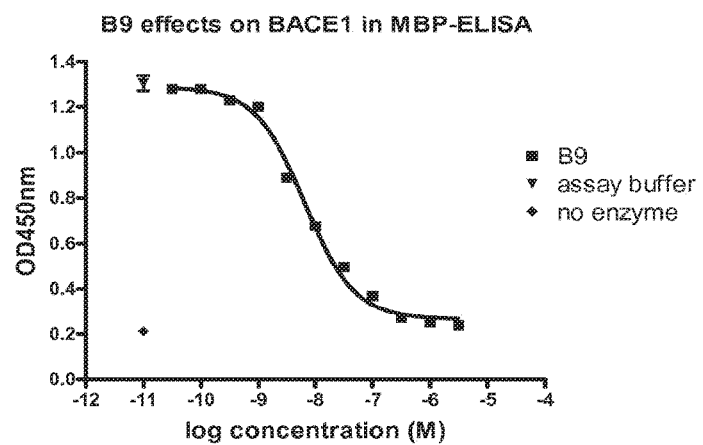
FIG. 9: Dose-response curve of Nb_B9 on BACE1 cleavage activity in MBP-ELISA using a big peptide substrate. In this cell-free enzymatic assay, Nb_B9 significantly inhibits BACE1 activity.

The contradictory results from B9 modulating BACE1 activity in opposite ways in the cellular assay and the FRET assay implicates that B9 might have different effects on BACE1 cleavage of a large substrate or a small substrate (APP as the cellular substrate for BACE1 contains 695 amino acids while the peptide substrate in FRET assay contains only ten amino acids). Therefore, it was tested whether B9 could inhibit BACE1 cleavage of a big substrate in another cell-free enzymatic assay MBP-ELISA, which uses the maltose binding protein connected to the C-terminal 125 amino acids of APPswe (MBP-APPswe-C125) as BACE1 substrate. As shown in FIG. 9, B9 inhibited BACE1 cleavage of MBP-APPswe-C125 in a dose-dependent manner, and could inhibit up to 95% of BACE1 activity. The results of this assay indicate that B9 is an inhibitor of BACE1 when using a big peptide substrate. So, V$_H$H Nb_B9, instead of being an active site binder, was more likely a steric inhibitor for BACE1. V$_H$H Nb_B9 could bind to an allosteric site on BACE1, thus stimulating BACE1 cleavage of small substrates that can still reach the cleavage site, but blocking access of big substrates, like APP to BACE1 by steric hindrance.

9. Affinity Analysis of the BACE1-Specific NANOBODIES®

The binding affinities of V$_H$Hs B9, 10C4 and 4A2 to human BACE1 ectodomain were analyzed by Biacore. As shown in Table 2 (left), B9 had the best affinity among the three inhibitory V$_H$Hs, with a Kd of 3.67 nM at pH 7.0. 10C4 and 4A2 had affinities of 74.7 nM and 48.2 nM, respectively, which are all within the normal range of affinities for V$_H$H antibodies.

Further, it was tested if the affinities of the V$_H$Hs were stable at pH 4.5, at which BACE1 has its optimal activity. As shown in Table 2 (right), there was no significant change in the affinities of the three V$_H$Hs at pH 4.5 compared to that in neutral pH, indicating that all three V$_H$Hs have binding affinities to BACE1 that were acidic stable.

TABLE 2

$V_HH$ affinities to human BACE1 at pH 7.0 and pH 4.5

| | pH 7.0 | | | pH 4.5 | | |
|---|---|---|---|---|---|---|
| | $k_{on}$ (M$^{-1}$s$^{-1}$) | $k_{off}$ (s$^{-1}$) | $K_D$ (nM) | $k_{on}$ (M$^{-1}$s$^{-1}$) | $k_{off}$ (s$^{-1}$) | $K_D$ (nM) |
| Nb_B9 | 2.67E+05 | 9.80E−04 | 3.67 | 6.62E+05 | 1.30E−03 | 1.96 |
| Nb_4A2 | 4.79E+05 | 2.31E−02 | 48.2 | 3.97E+05 | 8.41E−03 | 21.2 |
| Nb_10C4 | 1.06E+05 | 7.92E−03 | 74.7 | 4.51E+05 | 1.25E−02 | 27.7 |

The cross-reactivity of three $V_H$Hs to mouse BACE1 was investigated in anticipation of tests in primary cultures of mouse neurons. As shown in Table 3, both at neutral pH and acidic pH condition, all three $V_H$Hs cross-reacted with mouse BACE1, and their affinities to mouse BACE1 were within the same range of affinities as those measured with human BACE1.

TABLE 3

$V_H$H affinities to mouse BACE1 at pH 7.0 and pH 4.5

| | pH 7.0 | | | pH 4.5 | | |
|---|---|---|---|---|---|---|
| | $k_{on}$ (M$^{-1}$s$^{-1}$) | $k_{off}$ (s$^{-1}$) | $K_D$ (nM) | $k_{on}$ (M$^{-1}$s$^{-1}$) | $k_{off}$ (s$^{-1}$) | $K_D$ (nM) |
| Nb_B9 | 5.02E+05 | 8.90E−04 | 1.77 | 1.06E+06 | 1.18E−03 | 1.11 |
| Nb_4A2 | 1.65E+05 | 5.81E−03 | 35.2 | 2.51E+05 | 2.16E−03 | 8.61 |
| Nb_10C4 | 1.90E+05 | 7.97E−03 | 41.9 | 9.84E+05 | 9.88E−03 | 10 |

Figure 10:
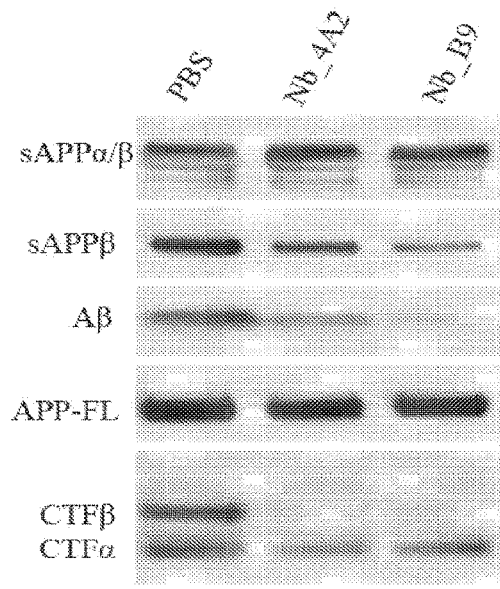
FIG. 10: $V_HH$s Nb_B9 (SEQ ID NO:6) and Nb_4A2 (SEQ ID NO:26) inhibit BACE1 cleavage of APPwt in primary cultured mouse neurons, as reflected in a decrease of Aβ, sAPPβ and CTFβ. Primary cultured neurons from wild-type mice were transduced with APPwt by Semliki Forest Virus (SFV), and then treated with purified Nb_B9 and Nb_4A2 by adding to the medium at a final concentration of 20 µM ($V_HH$s were first dissolved in PBS), neurons treated with PBS were used as a negative control. After a 16-hour treatment, conditioned medium and cell extract were analyzed by Western blot for APP-FL, CTFβ, CTFα, Aβ, sAPPβ and sAPPα/β.

10. BACE1-Specific NANOBODIES® Inhibit BACE1 Cleavage of APPwt in Primary Cultured Mouse Neurons $V_H$Hs Nb_B9 and Nb_4A2 were tested in the neuronal cell culture assay (FIGS. 10 and 11). Primary cultured neurons from wild-type mice were transduced with APPwt by Semliki Forest Virus (SFV), and then treated with purified $V_H$H Nb_B9 or Nb_4A2 by adding to the medium serial dilutions ($V_H$Hs were first dissolved and diluted in PBS). Neuron cultures were metabolic labeled for six hours. CTFβ, sAPPβ and Aβ were later analyzed as readout of BACE1 activity.

As shown in FIG. 10, Nb_B9 and Nb_4A2 inhibited BACE1 cleavage of APP reflected in the decrease of Aβ, sAPPβ, and CTFβ signals, while full-length APP and sAPPα levels remained at the same level as that of the control. The dose-response curve of Nb_B9 in neuron assay (FIG. 11) was established by quantification of the CTFβ level, which showed Nb_B9 inhibited BACE1 activity in a dose-dependent manner, with maximal inhibition effect around 57% BACE1 activity and the IC50 was around 500 nM.

11. Validation of BACE1-Inhibitory NANOBODIES® in Mouse Model

Camel single domain antibodies, the minimal-sized antibodies, which have superior properties for intracellular expression and function, including solubility, stability and functionality without the requirement for association between heavy and light chains of conventional antibodies, are candidate therapeutic molecules for in vivo gene delivery. The BACE1 inhibitory $V_H$H Nb_B9 is tested in a transgenic mouse model of Alzheimer's disease through viral vector-mediated gene delivery. Adeno-associated virus (AAV), one of the most effective vehicles for gene delivery to the central nervous system, is used in this experimentation. The cDNA of $V_H$H Nb_B9, fused with a signal peptide from BACE1 at its N-terminal and a Myc-tag at its C-terminal, was constructed into an AAV vector. The AAV vector used here contains a hybrid cytomegalovirus/chicken β-actin promoter and a wood-chuck post-transcriptional regulatory element, which is an optimized cassette for driving protein expression in neurons (Björklund et al., 2000).

For in vivo testing, Dutch-mutant APP transgenic mice are used, which overexpress E693Q-mutated human APP under the control of a neuron-specific Thy1 promoter element (Herzig et al., 2004). The E693Q Dutch mutation site on human APP is 21 amino acid residues behind BACE1 cleavage site, which does not interfere with APP processing by BACE1. Transgenic mice overexpressing the Dutch-mutant APP generate predominantly Aβ40 peptide, which is used as readout for BACE1 activity for in vivo test of $V_H$H Nb_B9. Two administrative routes, including stereotactic injection to the hippocampus region of adult mouse brain (Fukuchi et al., 2006) and intracranial injection to neonatal mouse brain (Levites et al., 2006) are used for the delivery of AAV vector packaged $V_H$H Nb_B9. AAV vector packaged GFP and $V_H$H Nb_B24 are used as negative controls.

Materials and Methods

Cell Culture

COS, BHK, MEF, CHO, HEK-APP$_{Sw}$, N2A and HeLa cells were cultured at 37° C. in a 5% $CO_2$ environment in Dulbecco's modified Eagle's medium/nutrient mixture F-12 (1:1) (Gibco) supplemented with 10% (v/v) Fetal Bovine Serum (FBS) (Hyclone). The HEK-APP$_{Sw}$ cells were kindly provided by Prof. C. Haass (Adolf Butenandt Institute, Ludwig-Maximilians University, Munich, Germany). For transient liposome-based transfections, a mix of FuGENE 6 (Roche Applied Science) and plasmid DNA with a ratio of 3:1 (in μl and μg, respectively) was added to a culture dish containing a 50% to 80% confluent monolayer of cells, according to the manufacturer's instructions. COS-hBACE1 stable cells were obtained after transient transfection of COS cells with pcDNA3.1zeo-hBACE1 and selection in 400 μg/ml zeocin (Invitrogen). SH-SYSY cells were grown in DMEM GLuTAMAX® 4500 mg/l D-glucose, 1 mM Sodium pyruvate (Gibco), supplemented with 15% (v/v) FBS.

Primary cortical neuronal cultures were isolated from E14 mouse embryos (according to Goslin and Banker, 1991). Briefly, dissected brain cortices were trypsinized with 0.25% trypsin in HBSS medium (Gibco), pelleted and transferred to DMEM (Invitrogen, San Diego, Calif.), supplemented with 10% (v/v) FBS and dissociated by passing them through Pasteur pipettes of decreasing diameters. Dispersed cells were collected by centrifugation and plated on poly-L-lysine (Sigma)-coated dishes and maintained in neurobasal medium (Gibco) supplemented with 0.5 μM L-glutamine (Invitrogen) and 2% (v/v) B27 Serum-free Supplement (Gibco). Cytosine arabinoside (5 μM) was added 24 hours after plating to prevent proliferation of glial cells.

Metabolic Labeling and Immunoprecipitation of APP Fragments

Cells were washed in Met-free or Met/Cys-free medium (GIBCO) and radioactively labeled in the appropriate medium containing, respectively, 100 μCi $^{35}$S Met or $^{35}$S Met/Cys (Trans $^{35}$S Label, MP Biomedicals, Irvine, Calif.). In case of incubations with FK-506, rapamycin and Nb_B26 (2.1 μM), compounds were added to the labeling medium. After six hours incubation, the culture supernatant was collected as a source of secreted Aβ or sAPPβ and centrifuged to remove detached cells. Cells were lysed in DIP buffer (20 mM Tris-HCl pH 7.4, 150 mM NaCl, 1% TRITON® X-100, 1% sodium desoxycholate, 0.1% SDS), except for the HEK-APP$_{Sw}$ cells, which were lysed in Tris buffered saline (TBS: 150 mM NaCl, 20 mM Tris-HCl, pH 7.5), containing 1% TRITON® X-100 and a cocktail of protease inhibitors (Complete, Roche). This lysis buffer still allows determination of protein concentration (Bio-Rad Protein Assay) to analyze efficiency of RNA interference on equal amounts of protein extract.

APP full-length and APP C-terminal stubs were precipitated from cell extracts using the APP C-terminal antibodies B63.1, B11/4 or B12/6 (1:200) and immunocomplexes were captured by protein G-sepharose. For Aβ species, samples of the cell-conditioned medium were incubated with either B7/8 or 4G8 (1:200). For the neurons overexpressing different BACE1 mutants, BACE1 proteins were precipitated from cell extracts with B45.1.

Immunoprecipitates were washed extensively in DIP buffer, followed by one washing step in TBS 1/3, eluted in LDS sample buffer (Invitrogen) supplemented with 1% β-mercapto ethanol and separated on 10% NuPAGE® gel (Novex) run in MES buffer for the APP fragments and MOPS for the BACE1 mutants. Gels were fixed, dried and exposed to a phosphor-imaging screen. Intensity of radioactive bands was quantified using PhosphorImaging (Typhoon, PerkinElmer) and the IMAGEQUANT® software package.

To detect sAPPβ, samples of conditioned medium were subjected to SDS-PAGE and Western blotting using B53/4 antibody.

Deglycosylation Experiments

Cells were harvested in Dulbecco's PBS (GIBCO), pelleted and lysed in 100 mM phosphate buffer at pH 5.8 for EndoH treatment (46% of 0.2 M $NaH_2PO_4$, 4% of 0.2 M $Na_2HPO_4$ and 50% water) and pH 7.4 for EndoF (9.5% of 0.2 M $NaH_2PO_4$, 40.5% of 0.2 M $Na_2HPO_4$ and 50% water), supplemented with 0.1% SDS, 0.5% TRITON® X-100, 0.5% β-mercapto-ethanol and protease inhibitors (Complete, Roche). Lysates were first denatured by heating them for 10 minutes at 70° C. and then treated with EndoH (1 unit/30 µl, Roche Applied Science) or EndoF (1 unit/30 µl, Roche Applied Science) for 19 hours at 37° C. and analyzed by SDS-PAGE and Western blotting.

Generation of Recombinant GST-Fusion Proteins pGEX-4T-1 plasmids (Pharmacia) encoding GST fusion proteins were introduced in BL21-competent cells (Merck Eurolab) and expression of the GST proteins was induced by 0.1 mM isopropyl β-D-thiogalactopyranoside (IPTG, Promega). Recombinant proteins were released from the bacteria by sonication in a Tris-saline buffer (150 mM NaCl, 10 mM Tris) containing a protease inhibitor cocktail (1 mM EDTA, 14 µg/ml aprotinin, 2 µg/ml pepstatin), 100 µg/ml lysozyme, 5 mM DTT and 0.5% N-laurylsarcosine (sarcosyl) (Frangioni and Neel, 1993). After centrifugation at 12500 rpm (Beckman J2-21M/E) to remove insoluble bacterial debris, TRITON® X-100 was added to a final concentration of 1% to neutralize the effects of the ionic detergent sarcosyl.

Immunization of a Dromedary and Llama and Analysis of the Immune Response

The immunization of dromedary and llama, the isolation of BACE1-binders and affinity measurements were done in collaboration with Prof. S. Muyldermans, VUB, Belgium.

With weekly intervals, a dromedary and llama were immunized six times subcutaneously with 150 µg of pure recombinant human BACE1 mixed with GERBU adjuvant (GERBU Biochemicals). The immunogen used for the immunization of the dromedary was provided by Dr. S. Masure (Johnson & Johnson Pharmaceutical Research & Development, Beerse, Belgium). In order to obtain large amounts of active recombinant BACE1, insect cells were infected with baculoviruses encoding BACE1 ectodomain (sBACE1) in which the four putative N-glycosylation sites were removed by substituting the respective Asn codons for Gln codons (Bruinzeel et al., 2002). The lack of glycosylation made it possible to produce a large, homogeneous pool of BACE1.

A llama was immunized with a different source of BACE1. In this case, the antigen was purified from sBACE1-overexpressing HEK293 cells (obtained from Prof. N. Mertens, Protein Service Facility, VIB, UGent) and, hence, resembled much better native, mature and thus fully glycosylated BACE1.

Forty-five days after the first injection, anticoagulated blood was collected. BACE1-specific antibody titers for each IgG subclass were analyzed using ELISA. The three individual IgG subclasses were first purified from serum based on their differential absorption on Protein A and Protein G and distinct elution conditions (Conrath et al., 2001a). Solid-phase coated BACE1 protein was incubated with serial dilutions of the different IgG subclasses and bound IgGs were subsequently detected with a rabbit anti-dromedary IgG antiserum and anti-rabbit IgG-alkaline phosphatase conjugates (Saerens et al., 2004).

Construction of a $V_HH$ Gene Fragment Library

Peripheral lymphocytes were isolated from the dromedary/llama sera (LYMPHOPREP®, NYCOMED®) and total RNA was extracted (according to Chomczynski and Sacchi, 1987). After RT-PCR with a $dN_6$ primer, the cDNA obtained was used as template for the amplification of a DNA fragment spanning the IgG variable domain until the CH2 domain, using primers CALL001 and CALL002 (see Table 4). These primers anneal to the IgG leader sequence and the CH2 exon of the heavy chain of all three IgG subclasses existing in dromedary, respectively. Using agarose gel extraction, the 600 bp fragment coming from heavy chain-only antibodies ($V_HH$-CH2, without CH1 domain) was separated from the 900 bp fragment derived from conventional antibodies ($V_H$-CH1-CH2 exons). $V_HH$ gene fragments were then amplified by PCR on the 600 bp DNA with a pair of nested primers, AE6 and FR4FOR (see Table 4). AE6 anneals to the $V_HH$ framework-1 and contains a Pst I site, whereas FR4FOR with a Not I site is complementary to the framework-4. The different $V_HH$ fragments were ligated into a pHEN4 phagemid vector and transformed into E. coli TG1 cells to create a library of $4 \times 10^7$ transformants. Colony PCR screening showed that approximately 90% of the colonies were transformed with a phagemid vector containing an insert with the size expected for a $V_HH$ fragment.

TABLE 4

Sequences of the different primers used for the $V_HH$ gene fragment library construction

| Primer | Sequence (5' to 3') | SEQ ID NO: |
|---|---|---|
| CALL001 | GTCCTGGCTGCTCTTCTACAAGG | 44 |
| CALL002 | GGTACGTGCTGTTGAACTGTTCC | 45 |
| AE6 | GATGTGCAGCTGCAGGAGTCTGGAGGAGG | 46 |
| FR4FOR | GGACTAGTGCGGCCGCTGCAGACGGTGACCTGGGT | 47 |

Selection of BACE1-Specific $V_HH$ Fragments

The $V_HH$ repertoire was expressed onto the surface of phages after rescuing the library with M13K07 helper phages. Specific $V_HH$s against BACE1 were enriched by three consecutive rounds of in vitro selection, a technique also known as panning (Smith and Petrenko, 1997). For this, the $V_HH$s were incubated on a solid phase coated with antigen. Unbound phages were washed away in PBS plus 0.05% TWEEN® 20 and bound phages were eluted with 100 mM triethylamine (pH 10.0). Eluted phage particles were immediately neutralized with 1 M Tris-HCl (pH 7.5) and used to re-infect exponentially growing E. coli TG1 cells. After the second and third round of selection, individual colonies were randomly picked.

Enzyme-Linked Immunosorbent Assay (ELISA)

Expression of the selected $V_HH$ was induced with 1 mM IPTG. The recombinant soluble C-terminally Hemagglutinin (HA)-tagged $V_HH$s (the gene encoding the HA-epitope is included in the pHEN4 phagemid vector) were extracted from the periplasm by an osmotic shock (200 mM Tris-HCl pH 8.0, 250 mM sucrose, 0.5 mM EDTA) (Skerra and Pluckthun, 1988) and tested for their capacity to recognize their antigen in ELISA tests. Maxisorb 96-well plates (Nunc) were coated overnight with BACE1 protein (100 µl of 1 µg/ml in PBS) at 4° C. Residual binding sites were blocked for two hours at room temperature with 1% (w/v) casein dissolved in PBS. This antigen-coated solid phase was then incubated with the different periplasmic extracts for one hour at room temperature. After washing, the solid phase was successively incubated with mouse anti-HA, alkaline phosphatase-conjugated anti-mouse (Sigma) and 2 mg/ml p-nitrophenyl phosphate (Sigma). Signals were analyzed at 410 nm.

Expression and Purification of $V_HH$s

The $V_HH$ genes of the clones scoring positive in ELISA were subcloned into the expression vector pHEN6, using Pst I and BstE II. Thereby, the HA-epitope tag at the C-terminus of the $V_HH$ molecules was replaced by a his6-tag. E. coli WK6 cells were transformed with the pHEN6 plasmids and expression of the recombinant soluble $V_HH$ proteins was induced by IPTG (Saerens et al., 2004). Soluble $V_HH$ molecules were extracted from the bacteria using an osmotic shock (Skerra and Pluckthun, 1988). The his-tagged recombinant proteins were then captured on a nickel-nitrilotriacetic acid superflow Sepharose column (QIAGEN®), eluted with an acetate buffer (pH 4.7), and additionally purified by size-exclusion chromatography.

BIAcore Measurements

The kinetic constants and affinity of the $V_HH$-antigen interactions were determined by surface plasmon resonance technology on a Biacore 3000 (Biacore AB). Purified $V_HH$ molecules, in a concentration range of 0-500 nM in Hepes Buffered Saline pH 7.0 or citrate buffer pH 5.0, were injected at 30 µl/minute onto BACE1 (500 resonance units), immobilized on a CM5 chip (according to De Genst et al., 2005). The kinetic and equilibrium constants ($k_{on}$, $k_{off}$ and $K_D$) were determined with the BIAevaluation v3.1 software (Biacore AB).

In Vitro FRET-Based Analysis of β-Secretase Activity

To determine whether the $V_HH$s affect BACE1 activity, an in vitro BACE1 FRET assay kit was used (Panvera P2985). This assay uses a synthetic BACE1 substrate that emits light upon cleavage. The amount of total fluorescence is linearly related to the cleavage rate of the substrate and hence to β-secretase activity. Reaction mixtures containing 20 nM of recombinant BACE1 enzyme and 250 nM of synthetic substrate were incubated with an excess of each $V_HH$ (2.2 µM) or the BACE1 inhibitor STA-200 (Enzyme System Products, 2.2 µM) in 50 mM sodium acetate, pH 4.5 at room temperature, protected from light. After two hours, fluorescence was measured at 595 nm using VICTOR 1420 multilabel counter (Perkin Elmer Life Sciences). For each $V_HH$, the background signal, emitted by a mix containing $V_HH$ and substrate but no enzyme, was subtracted from the signal measured for the mix containing $V_HH$, substrate and BACE1. As an alternative source of β-secretase activity, microsomal membranes were generated from HeLa cells ectopically expressing BACE1 as described hereinbefore. The resulting microsomal pellet was resuspended in 50 mM sodium acetate, pH 4.5. Fifty µg of microsomal proteins were mixed with 250 nM of the synthetic BACE1 substrate and 2.2 µM of $V_HH$ or STA-200. The enzymatic reaction and analysis were performed as before except that reactions were gently mixed every ten minutes during the two-hour incubation.

In another approach, FRET peptide substrate MCA-S-E-V-N-L-D-A-E-F-R-K(Dnp)-R-R-R-R-NH2 (SEQ ID NO:48) was synthesized by Ana Spec Inc. (San Jose, Calif., USA). Enzyme human BACE1 (1-460): IgGFc was purified from HEK293 cells according to the protocol described previously (Yang et al., 2004). For the reaction, enzyme was diluted in reaction buffer (50 mM Ammonium Acetate, pH 4.6, 3% BSA, 0.7% TRITON® X-100) at a concentration of 1 µg/ml, and substrate was diluted in reaction buffer at a concentration of 125 µM. Twenty µl $V_HH$ (diluted in reaction buffer) were mixed with 30 µl enzyme dilution and 50 µl substrate dilution in 96-well black polystyrene plates (Costar). The plates were read immediately for baseline signal with Envision (355 nm excitation, 430 nm emission, 1 second/well), followed by incubation overnight in the dark at room temperature. The plates were read the following morning using the same reader protocol; the FRET signal (-baseline signal) was used as the readout of enzyme activity in each reaction.

Co-Precipitation of Human BACE1 with His-Tagged $V_HH$s Using Ni-Beads

BACE1-overexpressing COS cells were lysed in PBS containing 1% TRITON® X-100 and protease inhibitors (1 µg/ml pepstatin, 14 µg/ml aprotinin, 0.5 mM PEFA-BLOC®). One hundred µg of this protein extract were incubated overnight at 4° C. with 2 of his-tagged $V_HH$ proteins and Ni-PDC beads (Affiland) in binding buffer (342 mM NaCl, 16.2 mM $Na_2HPO_4$, 6.7 mM KCl, 3.7 mM $KH_2PO_4$ with 1% TRITON® X-100) with the same protease inhibitors as used for cell lysis. The precipitates were washed in binding buffer supplemented with 10 mM imidazole, to reduce unspecific interactions, eluted using 300 imidazole and resolved by SDS-PAGE. BACE1 was visualized by Western blotting using a polyclonal rabbit anti-BACE1 antibody (ProSci Inc).

Phage Libraries Panning with Biotin-Labeled Antigen

Pannings of $V_HH$ phage library were performed with biotin-streptavidin system. Purified BACE1 ectodomain protein was labeled with Sulfo-NHS-SS-Biotin (Pierce) according to the manufacturer's protocol. $V_HH$ libraries were rescued with M13K07 helper phage to generate phages. For panning, $10^{11}$ phages were blocked with 1% BSA in 400 µl panning buffer (50 mM Tris-HCl pH 7.5, 150 mM NaCl, and 0.05% TWEEN® 20 for 30 minutes at RT. One hundred µl biotinylated BACE1 was added to phage to a final concentration at 200 nM. Phage and biotinylated BACE1 were incubated for one hour at RT with rotation. Meanwhile, 40 µl immobilized streptavidin (Pierce) were blocked in 1% BSA. After one-hour incubation, pre-blocked immobilized streptavidin were added to phage-biotinylated BACE1 solution and incubated for 40 minutes at RT with rotation. After incubation, immobilized streptavidin were spinned down by centrifugation at 3000 rpm for one minute, the supernatant containing unbound phage were discarded. The immobilized streptavidin were washed five times with 1 ml panning buffer; each wash lasted five minutes with rotation. After wash, 50 mM DTT were added to immobilized streptavidin and incubated for 40 minutes at RT with rotation. The immobilized streptavidin were spinned down and the supernatants containing eluted phages were used to re-infect E. coli TG1 cells for the next round of phage panning. After three rounds of consecutive panning, recovered phages were used to infect E. coli TG1 cells and plated out at $10^{-4}$ to $10^{-6}$ dilution, and single colonies were picked for further analysis.

Phage ELISA Screening

To generate phage particles with $V_H$Hs displayed on the surface for ELISA screening, single colonies from phage panning were inoculated in 2 ml 2× TY medium supplemented with 50 µg/ml ampicillin and 1% glucose in 24-well plates at 37° C. for eight hours with shaking at 220 rpm. After an eight-hour incubation, 5×10$^8$ pfu M13K07 helper phages were added to infect each well of bacterials. Infected bacterials were grown at 37° C. overnight with shaking at 220 rpm. The next morning, bacterials were spinned down by centrifugation at 3000 rpm for 20 minutes; supernatants containing phage particles were transferred into 24-well plates. Twenty percent PEG 6000/2.5 M NaCl were added to the supernatants using ⅙ volume to precipitate phage particles at 4° C. for 30 minutes. Phage particles were later retrieved by centrifugation at 3000 rpm for 30 minutes, and pellets were resuspended in 100 µl PBS.

For ELISA assay of phage particles, BACE1 ectodomain protein was coated on 48 wells of each 96-well microtiter plate at 100 ng/well at 4° C. overnight, the non-coated wells were used for control. The next morning, microtiter plates were blocked with 3% mild for one hour at RT. After blocking, 100 µl phage particles were added to each coated and non-coated well, and were incubated for two hours at RT. Plates were then washed five times with washing buffer (PBS, 0.05% TWEEN® 20). After wash, HRP-conjugated anti-M13 antibody (Amersham) was added to each well using 1:3000 dilution in 3% milk and incubated for one hour. Plates were then washed five times with washing buffer. After wash, developing substrate 0.02 mg/ml ABTS (Sigma) supplemented with 0.3% $H_2O_2$ (Sigma) were added to microtiter plates and incubated for 30 minutes at RT. Plates were read at OD405 nm with an ELISA reader.

Periplasmic Extract ELISA Screening

Expression vector pHEN4 containing a PelB (Pectate lysase) signal sequence before the $V_H$H cDNAs, thus $V_H$Hs are exported to the periplasmic space after expressed in bacterial system. To generate periplasmic extract containing $V_H$H proteins for ELISA test, single colonies from phage panning were inoculated in 1 ml Terrific Broth (TB) medium supplemented with 100 µg/ml ampicillin in 24-well plates at 37° C. with shaking at 220 rpm. When $OD_{600}$ reached 0.6, 1 mM IPTG was added to the culture to induce the expression of $V_H$H proteins. Bacterials were further incubated for 15 hours at 28° C. for protein expression. After the incubation, bacterials were harvested by centrifugation at 3000 rpm for 20 minutes, cell pellets were dissolved in TES solution (20 mM Tris-HCl pH 7.4, 1 mM EDTA, 250 mM sucrose) and incubated on ice for 30 minutes. The osmotic shock was given by adding 1.5× volume TES/4 to the bacterials and incubated on ice for 45 minutes. Supernatants containing $V_H$H proteins were collected by centrifugation at 300 rpm for 20 minutes and further used for ELISA. The ELISA assays followed the same protocol described above for phage ELISA. To detect $V_H$H proteins generated with a C-terminal HA tag, anti-HA monoclonal antibody (Amersham) was used as primary antibody and alkaline phosphatase conjugated goat anti-mouse antibody (Amersham) were used as secondary antibody. ELISA plates were developed with p-Nitrophenyl-phosphate (PNPP) substrate (Sigma) and read at OD 405 nm with an ELISA reader.

Adeno-Associated Virus (AAV) Construction and Preparation

For AAV generation, a standard method was followed (Levites et al., 2006). Briefly, the cDNA of $V_H$H Nb_B9, fused with a signal peptide from BACE1 at its N-terminal and a Myc-tag at its C-terminal, was constructed into an AAV vector containing a hybrid cytomegalovirus/chicken β-actin promoter and a woodchuck post-transcriptional regulatory element. AAVs were generated by plasmid transfection with helper plasmids in HEK293T cells. Forty-eight hours after transfection, the cells were harvested and lysed in the presence of 0.5% sodium deoxycholate and 50 U/ml Benzonase (Sigma) by freeze thawing, and the virus was isolated using a discontinuous iodixanol gradient purified on a HiTrap® HQ column (Amersham Biosciences). The genomic titer of virus was determined by quantitative PCR.

Mice

All animal experiments were in compliance with protocols approved by the local Animal Care and Use Committees. Dutch-mutant APP transgenic mice (C57BL/6J-TgN (Thy-APP$_{E693D}$)) were kindly provided by the laboratory of Mathias Jucker, University of Tubingen, Germany.

Stereotaxic Injections

In the first series of experiments, AAV vectors expressing $V_H$H Nb_B9 and GFP (negative control), and $V_H$H Nb_B24 (negative control) were administrated directly into the hippocampus of three-month-old Dutch-mutant APP transgenic mice. Mice were anesthetized with avertin and placed in a stereotaxic apparatus. AAV preparations were injected bilaterally (2 µl per site) into the CA3 region of the hippocampus (−2.0 mm antero-posterior from bregma, +/−2.3 mm mediolateral from bregma, and 1.7 mm below dura). Mice were then individually housed and allowed to recover from surgery. Their brains were processed for analyses five weeks after treatment.

Neonatal Injections

The procedure was described previously (Levites et al., 2006). Briefly, postnatal day 0 (P0) pups were cryoanesthetized on ice for five minutes. AAV preparations (2 µl) were injected intracerebroventricularly into both hemispheres using a 10 ml Hamilton syringe with a 30 gauge needle. The pups were then placed on a heating pad with their original nesting materials for three to five minutes and returned to their mother for further recovery. Their brains were processed for analyses three months after injection.

Tissue Preparation and Biochemical Analysis of Aβ

To analyze Aβ, the hippocampus (from stereotaxic injections) and the whole brains (from neonatal injections) were homogenized in Tissue Protein Extraction reagent (Pierce) supplemented with COMPLETE™ protease inhibitor and phosphatase inhibitor tablets (Roche Applied Science). The homogenized samples were centrifuged at 4° C. for one hour at 100,000×g, and the supernatant was used for immunoblot analysis and for Aβ ELISA measurements using ELISA kits (The Genetics Company).

REFERENCES

Arbabi Ghahroudi M., A. Desmyter, L. Wyns, R. Hamers, and S. Muyldermans 1997. Selection and identification of single domain antibody fragments from camel heavy-chain antibodies. *FEBS Lett.* 414:521-526.

Björklund A., D. Kirik, C. Rosenblad, B. Georgievska, C. Lundberg, and R. J. Mandel 2000. Toward a neuroprotective gene therapy for Parkinson's disease: use of adenovirus, AAV and lentivirus vectors for gene transfer of GDNF to the nigrostriatal system in the rat Parkinson model. *Brain Res.* 886:82-98.

Bruinzeel W., J. Yon, S. Giovannelli, and S. Masure 2002. Recombinant insect cell expression and purification of human beta-secretase (BACE-1) for X-ray crystallography. *Protein Expr. Purif.* 26:139-148.

Chomczynski P. and N. Sacchi 1987. Single-step method of RNA isolation by acid guanidinium thiocyanate-phenol-chloroform extraction. *Anal. Biochem.* 162:156-159.

Conrath K. E., M. Lauwereys, M. Galleni, A. Matagne, J. M. Frere, J. Kinne, L. Wyns, and S. Muyldermans 2001a. Beta-lactamase inhibitors derived from single-domain antibody fragments elicited in the camelidae. *Antimicrob. Agents Chemother.* 45:2807-2812.

Conrath K. E., U. Wernery, S. Muyldermans, and V. K. Nguyen 2003. Emergence and evolution of functional heavy-chain antibodies in Camelidae. *Dev. Comp. Immunol.* 27:87-103.

De Genst E., K. Silence, M. A. Ghahroudi, K. Decanniere, R. Loris, J. Kinne, L. Wyns, and S. Muyldermans 2005. Strong in vivo maturation compensates for structurally restricted H3 loops in antibody repertoires. *J. Biol. Chem.* 280:14114-14121.

Desmyter A., T. R. Transue, M. A. Ghahroudi, M. H. Thi, F. Poortmans, R. Hamers, S. Muyldermans, and L. Wyns 1996. Crystal structure of a camel single-domain VH antibody fragment in complex with lysozyme. *Nat. Struct. Biol.* 3:803-811.

Frangioni J. V. and B. G. Neel 1993. Solubilization and purification of enzymatically active glutathione S-transferase (pGEX) fusion proteins. *Anal. Biochem.* 210:179-187.

Fukuchi K., K. Tahara, H. D. Kim, J. A. Maxwell, T. L. Lewis, M. A. Accavitti-Loper, H. Kim, S. Ponnazhagan, and R. Lalonde 2006. Anti-Abeta single-chain antibody delivery via adeno-associated virus for treatment of Alzheimer's disease. *Neurobiol. Dis.* 23:502-11.

Goslin K. and G. Banker 1991. Rat hippocampal neurons in low-density culture. In *Culturing Nerve Cells*, MIT Press, Cambridge, Mass.

Herzig M. C., D. T. Winkler, P. Burgermeister, M. Pfeifer, E. Kohler, S. D. Schmidt, S. Danner, D. Abramowski, C. Stürchler-Pierrat, K. Bürki, S. G. van Duinen, M. L. Maat-Schieman, M. Staufenbiel, P. M. Mathews, and M. Jucker 2004. Abeta is targeted to the vasculature in a mouse model of hereditary cerebral hemorrhage with amyloidosis. *Nat. Neurosci.* 7:954-60.

Kabat E. A., T. T. Wu, H. M. Perry, K. S. Gottesman, and C. Foeller 1991. Sequences of proteins of immunological interest. US Public Health Services, NIH, Bethesda, Md.

Koo E. H. and S. L. Squazzo 1994. Evidence that production and release of amyloid beta-protein involves the endocytic pathway. *J. Biol. Chem.* 269:17386-17389.

Lauwereys M., M. Arbabi Ghahroudi, A. Desmyter, J. Kinne, W. Holzer, E. De Genst, L. Wyns, and S. Muyldermans 1998. Potent enzyme inhibitors derived from dromedary heavy-chain antibodies. *Embo. J.* 17:3512-3520.

Lesk A. M. and C. Chothia 1988. Elbow motion in the immunoglobulins involves a molecular ball-and-socket joint. *Nature* 335:188-190.

Levites Y., K. Jansen, L. A. Smithson, R. Dakin, V. M. Holloway, P. Das, and T. E. Golde 2006. Intracranial adeno-associated virus-mediated delivery of anti-pan amyloid beta, amyloid beta40, and amyloid beta42 single-chain variable fragments attenuates plaque pathology in amyloid precursor protein mice. *J. Neurosci.* 26:11923-8.

Lin X., G. Koelsch, S. Wu, D. Downs, A. Dashti, and J. Tang 2000. Human aspartic protease memapsin 2 cleaves the beta-secretase site of beta-amyloid precursor protein. *Proc. Natl. Acad. Sci. U.S.A.* 97:1456-1460.

Martin B. L., G. Schrader-Fischer, J. Busciglio, M. Duke, P. Paganetti, and B. A. Yankner 1995. Intracellular accumulation of beta-amyloid in cells expressing the Swedish mutant amyloid precursor protein. *J. Biol. Chem.* 270:26727-26730.

Muyldermans S., T. Atarhouch, J. Saldanha, J. A. Barbosa, and R. Hamers 1994. Sequence and structure of VH domain from naturally occurring camel heavy chain immunoglobulins lacking light chains. *Protein Eng.* 7:1129-1135.

Muyldermans S. and M. Lauwereys 1999. Unique single-domain antigen-binding fragments derived from naturally occurring camel heavy-chain antibodies. *J. Mol. Recognit.* 12:131-140.

Nguyen V. K., R. Hamers, L. Wyns, and S. Muyldermans 2000. Camel heavy-chain antibodies: diverse germline V(H)H and specific mechanisms enlarge the antigen-binding repertoire. *Embo. J.* 19:921-930.

Padlan E. A. 1994. Anatomy of the antibody molecule. *Mol. Immunol.* 31:169-217.

Saerens D., J. Kinne, E. Bosmans, U. Wernery, S. Muyldermans, and K. Conrath 2004. Single domain antibodies derived from dromedary lymph node and peripheral blood lymphocytes sensing conformational variants of prostate-specific antigen. *J. Biol. Chem.* 279:51965-51972.

Sinha S., J. P. Anderson, R. Barbour, G. S. Basi, R. Caccavello, D. Davis, M. Doan, H. F. Dovey, N. Frigon, J. Hong, K. Jacobson-Croak, N. Jewett, P. Keim, J. Knops, I. Lieberburg, M. Power, H. Tan, G. Tatsuno, J. Tung, D. Schenk, P. Seubert, S. M. Suomensaari, S. Wang, D. Walker, V. John, and et al. 1999. Purification and cloning of amyloid precursor protein beta-secretase from human brain. *Nature* 402:537-540.

Skerra A. and A. Pluckthun 1988. Assembly of a functional immunoglobulin Fv fragment in *Escherichia coli*. *Science* 240:1038-1041.

Smith G. P. and V. A. Petrenko 1997. Phage Display. *Chem. Rev.* 97:391-410.

Thinakaran G., D. B. Teplow, R. Siman, B. Greenberg, and S. S. Sisodia 1996. Metabolism of the "Swedish" amyloid precursor protein variant in neuro2a (N2a) cells. Evidence that cleavage at the "beta-secretase" site occurs in the golgi apparatus. *J. Biol. Chem.* 271:9390-9397.

Vassar R., B. D. Bennett, S. Babu-Khan, S. Kahn, E. A. Mendiaz, P. Denis, D. B. Teplow, S. Ross, P. Amarante, R. Loeloff, Y. Luo, S. Fisher, J. Fuller, S. Edenson, J. Lile, M. A. Jarosinski, A. L. Biere, E. Curran, T. Burgess, J. C. Louis, F. Collins, J. Treanor, G. Rogers, and M. Citron 1999. Beta-secretase cleavage of Alzheimer's amyloid precursor protein by the transmembrane aspartic protease BACE. *Science* 286:735-741.

Yan R., M. J. Bienkowski, M. E. Shuck, H. Miao, M. C. Tory, A. M. Pauley, J. R. Brashier, N. C. Stratman, W. R. Mathews, A. E. Buhl, D. B. Carter, A. G. Tomaselli, L. A. Parodi, R. L. Heinrikson, and M. E. Gurney 1999. Membrane-anchored aspartyl protease with Alzheimer's disease beta-secretase activity. *Nature* 402:533-537.

What is claimed is:

1. A single domain antibody, devoid of a light chain, that specifically binds beta secretase (BACE1) and inhibits BACE1 activity, wherein the single domain antibody comprises three complementarity determining regions (CDRs) comprising the amino acid sequences of SEQ ID NOS: 29, 30, and 31.

2. The single domain antibody of claim 1, wherein the single domain antibody is a VIM antibody.

3. The single domain antibody of claim 1, wherein the single domain antibody comprises four framework regions (FRs).

4. The single domain antibody of claim 3, wherein the four FRs and three CDRs are in sequence: FR1-CDR1-FR2-CDR2-FR3-CDR3-FR4.

5. The single domain antibody of claim 1, wherein the single domain antibody is bivalent.

6. The single domain antibody of claim 1, wherein the single domain antibody is bi-specific.

7. A composition comprising:
the single domain antibody of claim 1; and
at least one pharmaceutically acceptable carrier.

8. A method of treating a subject suffering from Alzheimer's disease, the method comprising:
administering the single domain antibody of claim 1 to the subject, so as to treat the subject.

9. A method of treating a subject suffering from Alzheimer's disease, the method comprising:
administering the composition of claim 7 to the subject, so as to treat the subject.

* * * * *

UNITED STATES PATENT AND TRADEMARK OFFICE
CERTIFICATE OF CORRECTION

PATENT NO. : 10,377,834 B2  
APPLICATION NO. : 15/872498  
DATED : August 13, 2019  
INVENTOR(S) : Bart De Strooper et al.

Page 1 of 1

It is certified that error appears in the above-identified patent and that said Letters Patent is hereby corrected as shown below:

In the Claims

In Column 65, Claim 2, Line 9, please remove "is a VIM antibody" and insert -- is a $V_HH$ antibody --

Signed and Sealed this  
Tenth Day of December, 2019

Andrei Iancu  
*Director of the United States Patent and Trademark Office*